(12) United States Patent
Bui et al.

(10) Patent No.: US 8,809,583 B2
(45) Date of Patent: Aug. 19, 2014

(54) METHODS FOR PRODUCING ISOMERS OF MUCONIC ACID AND MUCONATE SALTS

(75) Inventors: Vu Bui, Davis, CA (US); Man Kit Lau, Minnaepolis, MN (US); Doug MacRae, Okemos, MI (US); Dirk Schweitzer, Okemos, MI (US)

(73) Assignee: Amyris, Inc., Emeryville, CA (US)

( * ) Notice: Subject to any disclaimer, the term of this patent is extended or adjusted under 35 U.S.C. 154(b) by 43 days.

(21) Appl. No.: 13/518,534

(22) PCT Filed: Jan. 10, 2011

(86) PCT No.: PCT/US2011/020681
§ 371 (c)(1),
(2), (4) Date: Oct. 16, 2012

(87) PCT Pub. No.: WO2011/085311
PCT Pub. Date: Jul. 14, 2011

(65) Prior Publication Data
US 2013/0030215 A1    Jan. 31, 2013

Related U.S. Application Data

(60) Provisional application No. 61/335,638, filed on Jan. 8, 2010.

(51) Int. Cl.
*C07C 51/353* (2006.01)
*C12P 7/44* (2006.01)
*C12N 9/88* (2006.01)
*C12N 9/02* (2006.01)

(52) U.S. Cl.
CPC ............. *C12N 9/88* (2013.01); *C12N 9/0069* (2013.01); *C12P 7/44* (2013.01)
USPC .......................................... 562/591; 435/142

(58) Field of Classification Search
None
See application file for complete search history.

(56) References Cited

U.S. PATENT DOCUMENTS

| | | |
|---|---|---|
| 3,562,211 A | 2/1971 | Cassar et al. |
| 3,671,572 A | 6/1972 | Driscoll |
| 3,733,309 A | 5/1973 | Wyeth et al. |
| 3,789,078 A | 1/1974 | Nolan et al. |
| 3,940,431 A | 2/1976 | Wulf et al. |
| 4,024,173 A | 5/1977 | Lenz et al. |
| 4,028,307 A | 6/1977 | Ure |
| 4,074,062 A | 2/1978 | Murakami et al. |
| 4,126,755 A | 11/1978 | Bunger |
| 4,138,580 A | 2/1979 | Umemira et al. |
| 4,234,740 A | 11/1980 | Umemura et al. |
| 4,254,288 A | 3/1981 | Gladwin |
| 4,255,588 A | 3/1981 | Hillman |
| 4,260,810 A | 4/1981 | Umemura et al. |
| 4,535,059 A | 8/1985 | Hsieh et al. |
| 4,661,558 A | 4/1987 | Bell et al. |
| 4,731,328 A | 3/1988 | Maxwell |
| 4,827,072 A | 5/1989 | Imai et al. |
| 5,021,173 A | 6/1991 | Waddoups et al. |
| 5,145,987 A | 9/1992 | Molzahn et al. |
| 5,168,056 A | 12/1992 | Frost et al. |
| 5,208,365 A | 5/1993 | Fuchs et al. |
| 5,320,765 A | 6/1994 | Fetterman, Jr. et al. |
| 5,359,134 A | 10/1994 | Gustafson et al. |
| 5,367,096 A | 11/1994 | Ritter et al. |
| 5,412,108 A | 5/1995 | Fisher et al. |
| 5,420,227 A | 5/1995 | Pfeil et al. |
| 5,476,933 A | 12/1995 | Keana et al. |
| 5,487,987 A * | 1/1996 | Frost et al. .................... 435/142 |
| 5,616,496 A | 4/1997 | Frost et al. |
| 5,616,779 A | 4/1997 | Arndt |
| 5,744,671 A | 4/1998 | Beelen et al. |
| 6,013,297 A | 1/2000 | Endico |
| 6,171,797 B1 | 1/2001 | Perbost |
| 6,307,099 B1 | 10/2001 | Turner et al. |
| 6,323,373 B1 | 11/2001 | Spreitzer et al. |
| 6,355,817 B1 | 3/2002 | Woods et al. |

(Continued)

FOREIGN PATENT DOCUMENTS

| | | |
|---|---|---|
| DE | 526168 | 6/1931 |
| DE | 102007055242 | 5/2009 |

(Continued)

OTHER PUBLICATIONS

Elvidge, J. A.; Linstead, R. P.; Sims, Peter; Orkin, B. A. "Third isomeric (cis-trans) muconic acid" Journal of the Chemical Society (1950), 2235-41.*
Nishimura, Shigeo (2001). Handbook of Heterogeneous Catalytic Hydrogenation for Organic Synthesis. John Wiley & Sons., p. 68-72.*
Copending U.S. Appl. No. 12/816,701, filed Jun. 16, 2010 (008).
Achmatowicz et al., "O przydatnosci estru mukonowego do syntez dienowych. I. Kodensacja estru mukonoego z cyjamkiem winylu, akroleina I styrenem" Roczniki Chemi I Annales SAocietatis Chimicae Pokonorum, Jan. 1, 1958, 499-505, 32.

(Continued)

*Primary Examiner* — Jafar Parsa
*Assistant Examiner* — Amy C Bonaparte
(74) *Attorney, Agent, or Firm* — Greenberg Traurig, LLP; Fang Xie

(57) ABSTRACT

A method for producing cis,trans- and trans,trans-isomers of muconate by providing cis,cis-muconate produced from a renewable carbon source through biocatalytic conversion; isomerizing cis,cis-muconate to cis,trans-muconate under reaction conditions in which substantially all of the cis,cis-muconate is isomerized to cis,trans-muconate; separating the cis,trans-muconate; and crystallizing the cis,trans-muconate. The cis,trans-isomer can be further isomerized to the trans,trans-isomer. In one example, the method includes culturing recombinant cells that express 3-dehydroshikimate dehydratase, protocatechuate decarboxylase and catechol 1,2-dioxygenase in a medium comprising the renewable carbon source and under conditions in which the renewable carbon source is converted to 3-dehydroshikimate by enzymes in the common pathway of aromatic amino acid biosynthesis of the cell, and the 3-dehydroshikimate is biocatalytically converted to cis,cis-muconate.

22 Claims, 9 Drawing Sheets

(56) References Cited

U.S. PATENT DOCUMENTS

| | | |
|---|---|---|
| 6,392,088 B1 | 5/2002 | Bertola et al. |
| 6,428,767 B1 | 8/2002 | Burch et al. |
| 6,610,215 B1 | 8/2003 | Cai et al. |
| 6,646,155 B2 | 11/2003 | Herzog et al. |
| 6,916,950 B2 | 7/2005 | Gubisch et al. |
| 7,078,440 B2 | 7/2006 | Ishihara et al. |
| 7,169,588 B2 | 1/2007 | Burch et al. |
| 7,271,282 B1 | 9/2007 | Kawahara et al. |
| 7,282,601 B2 | 10/2007 | Kawahara et al. |
| 7,309,754 B2 | 12/2007 | Brock et al. |
| 7,319,161 B2 | 1/2008 | Noe et al. |
| 7,385,081 B1 | 6/2008 | Gong |
| 7,531,593 B2 | 5/2009 | Sunkara et al. |
| 2002/0026070 A1 | 2/2002 | Bertola et al. |
| 2004/0054220 A1 | 3/2004 | Noe et al. |
| 2005/0038283 A1 | 2/2005 | Kawahara et al. |
| 2005/0067373 A1 | 3/2005 | Brock et al. |
| 2007/0129565 A1 | 6/2007 | Sutton et al. |
| 2009/0065736 A1 | 3/2009 | Johnson et al. |
| 2009/0099368 A1 | 4/2009 | Kotrel et al. |
| 2009/0124829 A1 | 5/2009 | Gong |
| 2009/0312470 A1 | 12/2009 | Bradshaw et al. |

FOREIGN PATENT DOCUMENTS

| | | |
|---|---|---|
| EP | 0450512 | 1/1995 |
| EP | 0569823 | 8/1996 |
| EP | 1347005 | 9/2003 |
| EP | 0971870 | 10/2003 |
| EP | 1386937 | 2/2004 |
| EP | 1683819 | 7/2006 |
| EP | 1736497 | 12/2006 |
| FR | 2418807 | 9/1979 |
| GB | 1021520 | 3/1966 |
| GB | 1022870 | 3/1966 |
| WO | 9615112 | 5/1996 |
| WO | 9732913 | 9/1997 |
| WO | 9838150 | 9/1998 |
| WO | 9940049 | 8/1999 |
| WO | 2009064515 | 5/2009 |
| WO | 2010148049 | 12/2010 |
| WO | 2011085311 | 7/2011 |

OTHER PUBLICATIONS

Alder et al. "Darstellung ung Sterochemie Der 1.2.3A Tetracarbonsauren Des Cyclopentans Und Cuclohexans," Justus Liebigs Annalen Der Chemie, Jan. 27, 1958, 7-32, 611.1.
Anzalone et al. "Substituent Effects on Hydrogenation of Aromatic Rings: Hydrogenation vs. Hydrogenolysis in Cyclic Analogous of Benzyl Ethers" Journal of Organic Chemistry, Jan. 1, 1985. 50, 1.
Avram et al. "Investigation in the cyclobutane series X: Some reactions of dibenzotricyclo-octadiene and of dibenzocyclo-octatetraene," Tetrahedron, 1963, 309-317, 19, 2.
Bachmann et al., "The Diels-Alder Reaction of 1-Vinylapthulene with alpha, beta- and, beta, gamma, delta- Unsaturated Acids and Derivatives," Journal of the American Chemical Society, Sep. 1, 1949,3062-3072, 71, 9.
Baeyer, "Uber Die Constitution Des Benzols," Justus Liebigs, Annalen Der Chemie, 1888, 103-190, 245.
Bolchi et al., "Peptidomimetic inhibitors of farnesyltransferase with high in virto activity and significant cellular potency," Bioorganic & Medical Chemistry Letters, Oct. 12, 2007, 6192-6196, 17, 22.
Burdett, "An Improved Acid Chloride Preparation via Phase Transfer Catalysis," Synthesis, Jun. 1991, 441-442, 6.
Chang et al., "Synthesis and binding properties of a macrocyle with two binding subcavities," Tetrahedron Letters, Jun. 19, 2006, 4141-4144, 47, 25.
Cook et al., Conformation analysis of substituted 1, 2-dihyronaphthalenes, Journal of the Chemical Society, Jan. 1, 1972, 1901-1905.
Deno, "The Diels-Alder Reaction with alpha, beta, gamma, delta-Unsaturated Acids," Journal of the American Chemical Society, Sep. 1, 1950, 4057-4059, 72, 9.

Dewar et al., "Factors influencing Stabilities of nematic liquid crystals," Journal of the American Chemical Society, Nov. 1975, 6658-6662, 97, 23.
Elvidge et al., "The third isometric (cis-trans-) muconic acid," Journal of Chemistry Society (Resumed), 1950, 2235-2241.
Freund et al., "Synthese von Indandionen," Justus Liebigs Annalen Der Chemie, 1916, 14-38, 411, 1.
Gajewski et al., "Deuterium kinetic isotope effects in the 1, 4-dmiethylenecyclohexane boat Cope rearrangement," Journal of the American Chemical Society, Feb. 1986, 108, 3.
Grundmann, Zur Kenninis der Oxydation von Phenolen mit Peressigsaure, Berichte Der Deutschen Chemischen Gesellschaft, Jul. 8, 1936, 1755-1757, 69, 7.
Kaufmann et al., "Diels-Alder-Reaktionen auf dem Fettgebiet VIII Die Reaktion von Polyenfettsäuren und trocknenden Ölen mit Acetylen; eine neue Synthese derneue Terephthalsäure," Fette, Sceifen, Anstrichmittel, 1963, 856-858, 65, 10.
Korver et al., "The diels-alder reaction of styrene with trans-penta-1,3-diene: Methyl 2-trans, 4-pentadienoate and dimethyl 2-trans, 4-trans-hexadiendioate," Tetrahedron, 1969, 4109-4115, 25, 17.
Koshel et al., Liquid-phase Catalytic Oxidation of 2,5-Dimethylbiphenyl, Russian Journal of Organic Chemistry, Jan. 1, 2001, 877-880, 37, 6.
Lee et al., "Photochemistry of bicycle [2.2.2.] ocetones: an uncommon oxidative decarbonylation," Chemical Communication, 1999, 801-802, 1999, 9.
Lyszczek, "Thermal and spectroscopic investigations of new lanthanide complexes with 1,2,4-benzenetricarboxylic acid," Journal of Thermal Analysis and Calorimetry, Apr. 29, 2007, 533-539, 90, 2.
McMillan et al., "Hexamthylene-1,6-bis-t-amines in which Part of the Six Carbon Chain is also Part of the Six-member Ring," Journal of the American Chemical Society, Aug. 1956, 78, 16.
Meshram et al., "Zinc Promoted Convennient and General Symthesis of Thiol Esters," Synlett, Aug. 1, 1998, 877-878.
Morrison, "A Synthesis of Flurene-3-carboxylic Acid," The Journal of Organic Chemistry, Sep. 1958, 23, 9.
Roll et al., "Proton magnetic resonance spectra and stereochemistry of some 5,6-disubtituted bicycle[2.2.2.] oct-2-enes," Journal of Pharmaceutical Sciences, Aug. 1965, 11110-1117, 54, 8.
Shimasaki et al., "Retinodal Dienamides and Related Aromatic Amides. Replacement of the 9-ene Structure of Retinoic Acid with a Trans- or Cis-Amide Group," Chemical and Pharmaceutical Bulletin, Jan. 1, 1995, 100-107, 43, 1.
Sih et al., "The naphthalene route to anthracyclinones," Tetrahedron Letters, 1979, 1285-1288, 20-15.
Wintersteiner et al., "Degradation of Vertramine to Benzene- 1, 2, 3, 4-Tetracarboxylic Acid," Journal of American Chemical Society, Jun. 1953, 2781-2782, 75, 11.
Yagupol'skii, et al., "Fluorination of aromatic carboxylic acids by sulfur tetrafluoride," Journal of Organic Chemistry USSR, (English Translation), 1973, 710-716, 9.
Zuercher et al., "Tandem ring opening-ring closing metathesis of cyclic olefins," Journal of the American Chemical Society, Jan. 1, 1996, 6634-6640, 118, 28.
Achmatowicz et al. "Using Muconic Ester for Diene Synthesis. I. Condensation of Muconic Ester with Vynil Cyanide, Acrolein, and Styrene" Roczniki Chemii, vol. 32, p. 499-511 (1958).
Alder et al."Presentation and Stereochemistry of the 1.2.3.4 Tetracarboxylic Acids of Cyclpentane and Cyclohexane" Institute of Chemistry of the University of Cologne on the Rhine, Aug. 6, 1957.
Isoda et al. "Medicinal Chemical Studies on Antiplasmin Drugs. III. 4-Aminomethylcyclohexanecarboxylic Acid and its Derivatives having a Methyl Group," Chem. Pharm. Bull. vol. 27, pp. 2735-2742 (1979).
Kaufmann et al. "Diels-Alder Reactions in the Field of Fats VIII: The Reaction of Polyene Fatty Acids and Drying Oils with Acetylene: A New Synthesis of Terephthalic Acid," Institute for Industrial Fat Research, Munster (Westphalaia).
Gaal, A et al. "Cis, Cis-Muconate Cyclase from Trichosporon Cutanem," The Biochemical Journal. vol. 191, No. 1, Oct. 1, 1980.
Wu, C M et al. "Microbial Synthesis of Cis, Cis-Muconic acid by *Sphingobacterium* sp. CGC Generated from Effluent of a Styrene

(56) References Cited

OTHER PUBLICATIONS

Monomer (SM) Production Plant," Enzyme and Microbial Technology, vol. 35, No. 6-7. Dec. 1, 2004.

Wu, C M et al "Microbial Synthesis of Cis, Cis-Muconic Acid from Benzoate by *Sphingobacterium* Sp. Mutants," Biochemical Engineering Journal. vol. 29, No. 1-2. Apr. 1, 2006.

Parke DV et al. "Studies in Detoxication: The Metabolism of Benzene. The Muconic Acid Excreted by Rabbits Receiving Benzene Determination of the Isomeric Muconic Acids," The Biochemical Journal. vol. 51, pp. 339-348. Jun. 30, 1952.

Achmatowicz et al., "The Application of Muconic Ester to Diene Additions," 3 Bulletin de l'Academie Polonaise des Sciences 557-564 (1955).

Jerry March, Advanced Organic Chemistry Reactions Mechanisms, and Structure 1073-1074 (Robert H. Summersgill and Anne T. Vinnicombe eds., McGraw-Hill, Inc. 1977) (1968).

Alder et al., "Uber den Sterischen Verlauf von Dien-Synthesen mit Acyclischen Dienen," 571 Justua Lieb. Ann. Chem. 153-157 (1950).

Niue et al., "Benzene-Free Synthesis of Adipic Acid," 18 Michigan State University, Department of Chemistry, Biotechnological Program 201-211 (2002).

Somorjai, Gabor A., "The 13th International Symposium on Relations Between Homogeneous and Heterogeneous Catalysis—An Introduction," Lawrence Berkeley National Laboratory (2008). Available at the eScholarship Repository, University of California: http://repositories.cdlib.org/lbnl/LBNL-1226E.

Database ChEBI [Online] EBI; Sep. 14, 2006 "trans, trans-muconate", XP002627174, retrieved from www.ebi.ac.uk/chebi acession No. 27035.

Database ChEBI [Online] EBI; Sep. 14, 2006 cis, trans-muconate, CP002627173, retrieved from www.ebi.ac.uk/chebi acession No. 27031.

International Search Report in International Application No. PCT/US2011/020681 mailed Apr. 4, 2011.

Farmer et al., "Properties of Conjucated Compounds," J. Chemical Society 897-909 (1929).

Copending U.S. Appl. No. 12/816,600, filed Jun. 16, 2010 (003).
Copending U.S. Appl. No. 12/816,763, filed Jun. 16, 2010 (006).
Copending U.S. Appl. No. 12/816,742, filed Jun. 16, 2010 (007).

* cited by examiner

METHODS FOR PRODUCING ISOMERS OF MUCONIC ACID AND MUCONATE SALTS

RELATED APPLICATIONS

This application is a National Phase application of International Application No. PCT/US2011/020681 filed Jan. 10, 2011, which claims the benefit of and priority to U.S. Provisional Patent Application No. 61/335,638, filed Jan. 8, 2010, the disclosures of each of which applications are incorporated herein by reference in their entirety.

FIELD OF THE INVENTION

The invention relates generally to the biological production of muconate from renewable feedstock. The invention relates more particularly to the production of muconate isomers, as well as precursors and derivatives thereof, from a renewable biomass-derived carbon source.

BACKGROUND OF THE INVENTION

Worldwide consumption of dimethyl terephthalate (DMT) is projected to average to 3.97 million metric tons by 2012. DMT is an ester of terephthalic acid and methanol and is used in the production of polyesters, including polyethylene terephthalate and polytrimethylene terephthalate. DMT is also a primary ingredient used in the manufacture industrial plastics, automotive parts, films, fishing lines, and food packaging materials.

Traditionally, DMT production utilizes the esterification of terephthalic acid with methanol generated by catalytic homogeneous oxidation of paraxylene. For example, liquid paraxylene can be oxidized by air in the presence of a cobalt salt catalyst to form an oxidate containing p-toluic acid and monomethyl terephthalate, and esterification can be carried out in the presence of methanol to form DMT.

Trimellitic acid (TMA) is another commercially important product with applications as an intermediate in the chemical industry, including resins for powder coatings, inks, wire enamels, high performance plasticizers with low volatility, and engineering polymers for high temperature applications. TMA can also be dehydrated to produce trimellitic anhydride, which is another commercially important starting material for the production of polymers and chemical intermediates.

Traditionally, TMA is produced by oxidation of pseudocumene (1,2,4-trimethylbenzene). Terephthalic acid and isophthalic acid can be produced commercially by liquid phase oxidation of p-xylene or m-xylene in the presence of acetic acid as a solvent and of a catalytic system including cobalt, manganese and bromine.

These processes, like the processes for producing many other commercially important chemical precursors, intermediates, and products, can be undesirable due to a heavy reliance upon environmentally sensitive and non-renewable feedstocks (e.g., petroleum feedstocks), and their propensity to yield undesirable by-products (e.g., greenhouse gases, heavy metals, halogens, carcinogenic hydrocarbons). As such, a need exists for improved methods and systems that utilize renewable feedstocks to produce DMT, TMA, as well as other chemical products.

As described in U.S. Publication No. 2010/0314243 by Frost et al. and International Publication No. 2010/148049 by Frost et al., the disclosures of both of which applications are incorporated herein by reference in their entirety, DMT and TMA can be produced from muconic acid. In addition, muconic acid, also known as 2,4-hexadienedioic acid, due to its double bonds and diacid functionality, can undergo a wide variety of reactions. Many muconic acid derivatives are known, including lactones, sulfones, polyamides, polyesters, thioesters, addition polymers, and other compounds. Such compounds have a wide variety of uses, including use as surfactants, flame retardants, UV light stabilizers, thermoset plastics, thermoplastics and coatings. Thus, improved methods for biological production of muconic acid or muconate from renewable feedstock are highly desirable for producing DMT, TMA and other chemicals.

SUMMARY OF THE INVENTION

The description of the invention uses the terms "muconate" and "muconic acid." The term "muconic acid" refers to the chemical species in which both carboxylic acid function groups are protonated, and the molecule is formally a neutral species. Muconic acid has the chemical formula HOOC—CH=CH—CH=CH—COOH. The term "muconate" refers to the corresponding deprotonated chemical species in which one or both of the carboxylic acid function groups is deprotonated to give the anionic or doubly-anionic form which would be the predominate chemical species at physiological pH values. However, as the terms "muconic acid" and "muconate" refer to the protonated or deprotonated forms of the same molecule, the terms are used synonymously where the difference between protonated and deprotonated (e.g., non-ionized and ionized) forms of the molecule is not usefully distinguished.

The present invention provides methods for the production the three isomers of muconate, that is, the cis,cis; cis,trans; and trans,trans isomers as well as precursors and derivatives thereof, from biomass-derived carbon sources. The isomers structurally differ by the geometry around the two double bonds. In addition, the isomers can have different physical properties (e.g., melting point) and chemical reactivities. The methods can include microbial biosynthesis of products from readily available carbon sources capable of biocatalytic conversion to erythrose 4-phosphate (E4P) and phosphoenolpyruvate (PEP) in microorganisms having a common pathway of aromatic amino acid biosynthesis.

One preferred carbon source is D-glucose. Advantageously, D-glucose and other carbon sources useable in connection with the present invention are non-toxic. Furthermore, such carbon sources are renewable, being derived from starch, cellulose, and sugars found in corn, sugar cane, sugar beets, wood pulp, and other biomass resources.

Host microbial organisms suitable for facilitating various steps in the present invention can be selected from genera possessing an endogenous common pathway of aromatic amino acid biosynthesis. Preferred host organisms include mutant strains of *Escherichia coli* genetically engineered to express selected genes endogenous to *Klebsiella pneumoniae* and *Acinetobacter calcoaceticus*. One preferred *E. coli* mutant for use in this invention is *E. coli* AB2834, an auxotrophic mutant which is unable to catalyze the conversion of 3-dehydroshikimate (DHS), an intermediate along the common pathway of aromatic amino acid biosynthesis, into shikimic acid due to a mutation in the aroE locus which encodes the enzyme shikimate dehydrogenase.

The common pathway of aromatic amino acid biosynthesis produces the aromatic amino acids phenylalanine, tyrosine, and tryptophan in bacteria and plants. The common pathway ends with the molecule chorismate, which is subsequently converted into phenylalanine, tyrosine, and tryptophan by three separate terminal pathways.

Approaches for increasing the efficiency of production of the common amino acid biosynthetic pathway include those described in U.S. Pat. No. 5,168,056, issued Dec. 1, 1992, in U.S. Pat. No. 5,616,496 issued Apr. 1, 1997, and in U.S. Ser. No. 07/994,194, filed Dec. 21, 1992 and now abandoned, the disclosures of all of which are hereby incorporated by reference in their entirety.

In using the genetically engineered host organisms, carbon flow directed into aromatic amino acid biosynthesis can proceed along the common pathway to yield elevated intracellular levels of DHS, which accumulates due to a mutation along the common pathway of aromatic amino acid biosynthesis, which prevents the conversion of DHS to chorismate. The DHS serves as a substrate for the enzyme 3-dehydroshikimate dehydratase (aroZ), and action of this enzyme on DHS produces protocatechuate. Protocatechuate is thereafter converted to catechol via another enzyme known as protocatechuate decarboxylase (aroY). The catechol thus formed is in turn converted to cis,cis-muconic acid by the action of the enzyme catechol 1,2-dioxygenase (catA).

The three enzymes catalyzing the biosynthesis of cis,cis-muconate from DHS, that is, aroZ, aroY, and catA, can be expressed in a host cell using recombinant DNA comprising genes encoding these three enzymes under control of a suitable promoter. Carbon flow can be thereby forced away from the pathway of aromatic amino acid biosynthesis and into the divergent pathway to produce cis,cis-muconate. The cis,cis-muconic acid thus formed can accumulate in the extracellular medium which can be separated from the cells by centrifugation, filtration, or other methods known in the art. The isolated cis,cis-muconic acid can thereafter be chemically hydrogenated to yield adipic acid.

In various embodiments of the invention, after the cis,cis-muconate has been produced, it can subsequently be isomerized to cis,trans-muconate or trans,trans-muconate, both of which have differing physical properties and chemical reactivity which can give utility different from or beyond that of cis,cis-muconate. For example, cis,trans-isomer can have greater solubility than cis,cis-muconate in aqueous and/or organic media, allowing advantageous recovery and processing. As a further example, the trans,trans-isomer can have unique utility over the cis,cis-isomer as a reactant in Diels-Alder reactions.

In one aspect, the invention features a method for producing cis,trans-muconate. The method comprises providing cis,cis-muconate produced from a renewable carbon source through biocatalytic conversion (e.g., utilizing the aroZ, aroY, and catA enzymes), isomerizing cis,cis-muconate to cis,trans-muconate under reaction conditions in which substantially all of the cis,cis-muconate is isomerized to cis,trans-muconate, separating the cis,trans-muconate, and crystallizing the separated cis,trans-muconate (e.g., as the protonated cis,trans-muconic acid).

In another aspect, the invention features a method for producing cis,trans-muconate. The method comprises: providing a fermentation broth comprising cis,cis-muconate produced from a renewable carbon source through biocatalytic conversion; isomerizing cis,cis-muconate to cis,trans-muconate under reaction conditions in which substantially all of the cis,cis-muconate is isomerized to cis,trans-muconate; separating the cis,trans-muconate from the broth; and crystallizing the cis,trans-muconate.

In yet another aspect, the invention features cis,trans-muconate produced by a method featured by the invention. The cis,trans-muconate can be recovered as a salt, for example, an inorganic salt such as sodium, calcium, or ammonium muconate.

In yet another aspect, the invention features a method for producing trans,trans-muconate that includes isomerizing cis,cis-muconate produced from a renewable carbon source through biocatalytic conversion to trans,trans-muconate under reaction conditions in which substantially all of the cis,cis-muconate is isomerized to trans,trans-muconate. For example, the isomerization reaction can be catalyzed by a precious metal hydrogenation catalyst, by a sponge metal hydrogenation catalyst, or by a skeletal hydrogenation catalyst.

In yet another aspect, the invention features a method for producing trans,trans-muconate that includes isomerizing cis,trans-muconate produced from a renewable carbon source through biocatalytic conversion to trans,trans-muconate under reaction conditions in which substantially all of the cis,trans-muconate is isomerized to trans,trans-muconate. For example, the isomerization reaction can be catalyzed by a precious metal hydrogenation catalyst, by a sponge metal hydrogenation catalyst, or by a skeletal hydrogenation catalyst.

In still another aspect, the invention features trans,trans-muconate produced by a method featured by the invention (e.g., renewable trans,trans-muconate).

In other examples, any of the aspects above, or any method, apparatus, or composition of matter described herein, can include one or more of the following features.

In various embodiments, the method includes culturing recombinant cells that express 3-dehydroshikimate dehydratase (e.g., aroZ), protocatechuate decarboxylase (e.g., aroY) and catechol 1,2-dioxygenase (e.g., catA) in a medium comprising a renewable carbon source and under conditions in which such renewable carbon source is converted to DHS by enzymes found in the common pathway of aromatic amino acid biosynthesis of the cell, and the resulting DHS is biocatalytically converted to cis,cis-muconate.

The production of cis,cis-muconate by the fermentation of the renewable carbon source can produce a broth comprising the recombinant cells and extracellular cis,cis-muconate. The production can also include the step of separating the recombinant cells, cell debris, insoluble proteins and other undesired solids from the broth to give a clarified fermentation broth containing substantially all, or most of, the cis,cis-muconate formed by the fermentation. The cis,cis-muconate can then be isomerized to cis,trans-muconate in the clarified fermentation broth.

In certain embodiments, a fermentation broth comprising cis,cis-muconate produced from a renewable carbon source through biocatalytic conversion can be provided for producing cis,trans-muconate or trans,trans-muconate. The fermentation broth can include recombinant cells that express 3-dehydroshikimate dehydratase, protocatechuate decarboxylase and catechol 1,2-dioxygenase. In some embodiments, the fermentation broth is provided in a vessel and the isomerization reaction is carried out in the vessel. The vessel can be a fermentor vessel. In some examples, recombinant cells that express 3-dehydroshikimate dehydratase, protocatechuate decarboxylase and catechol 1,2-dioxygenase can be cultured in a medium comprising the renewable carbon source and under conditions in which the renewable carbon source is converted to 3-dehydroshikimate by enzymes in the common pathway of aromatic amino acid biosynthesis of the cell, and the 3-dehydroshikimate is biocatalytically converted to cis,cis-muconate. For example, the recombinant cells can be cultured in the fermentor vessel, thereby producing the fermentation broth. Additionally, the recombinant cells can be removed from the fermentation broth as desired.

In some embodiments, the isomerization reaction is catalyzed by an acid. The acid can be an inorganic acid (e.g., mineral acid) or an organic acid. An acid can be applied to the process in either a hydrated or anhydrous form. In one example, a salt byproduct can be ammonium sulfate, which can be subsequently used, for example, as a fertilizer. The isomerization reaction can be carried out at a pH between about 1.5 and about 6.5 (e.g., 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5). Preferably, the isomerization reaction can be carried out at a pH between about 3.5 and about 4.5.

In certain embodiments, the isomerization reaction is carried out at a temperature of about 47° C. or greater (e.g., 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or higher). Preferably, the isomerization reaction can be carried out at a temperature of about 60° C. or greater. The isomerization reaction can be substantially complete within 8, 7.75, 7.5, 7.25, 7, 6.75, 6.5, 6.25, 6, 5.75, 5.5, 5.25, 5, 4.75, 4.5, 4.25, 4, 3.75, 3.5, 3.25, 3, 2.75, 2.5, 2.25, 2, 1.75, 1.5, 1.25, 1, 0.75, 0.5, or 0.25 hours.

In various embodiments, the isomerization reaction proceeds substantially without precipitation of cis,trans-muconate from the reaction mixture. In certain embodiments, the isomerization reaction includes monitoring the isomerization of cis,cis-muconate to cis,trans-muconate. In some embodiments, the isomerization reaction is carried out at a pressure above about atmospheric pressure.

In various embodiments, after isomerization, the cis,trans-muconate can be separated from the solution, medium, broth, or fermentation broth by further acidification sufficient to cause the cis,trans-muconic acid to precipitate. The broth can be acidified to a pH below about 3.0 (e.g., 2.9, 2.8, 2.7, 2.6, 2.5, 2.4, 2.3, 2.2, 2.1, 2, or lower). The broth can be further acidified to a pH below about 2.

In certain embodiments, the separating step includes cooling the solution to a temperature below about 37° C., below about 25° C., below about −4° C., or below about −20° C.

In certain embodiments, the separating step comprises centrifugation, filtration, or other physical processes for separating the precipitated cis,trans-muconic acid. In various embodiments, the separating step includes extracting the cis,trans-muconate from the fermentation broth using an organic solvent. The organic solvent can include one or more of methanol, ethanol, propanol, isopropanol, butanol, acetic acid, acetonitrile, acetone, and tetrahydrofuran, tert-butyl methyl ether, methyl tetrahydrofuran, cyclohexanone or cyclohexanol, or mixtures of these. In one embodiment, the extraction can be carried out at a pH of between about 7 and 4 (e.g., about 7, 6.75, 6.5, 6.25, 6, 5.75, 5.5, 5.25, 5, 5.75, 5.5, 5.25, 4) without significant precipitation of the cis,trans-muconic acid, and can include the use of automated addition of acid to maintain the pH in this region as the extraction proceeds. In another embodiment, the extraction step can be carried out at a pH below about 4 (e.g., about 4, 3.75, 3.5, 3.25, 3, 2.75, 2.5, 2.25, 2) in the presence of precipitated cis,trans-muconic acid which is dissolved by the organic solvent. In still another embodiment, the extraction step can be performed without first removing cells, cell debris, proteins, or other undesired materials from the fermentation broth. In yet another embodiment, the extraction step can be mediated by a membrane.

In certain embodiments, the cis,cis-muconate can first be removed from the fermentation broth, and then subjected to the isomerization, separation, and purification steps. Such removal can be accomplished by extraction, precipitation, ion-exchange chromatography, selective membrane separation, electrodialysis, or other methods known in the art.

In some embodiments, the cis,trans-muconic acid is purified by crystallization using an organic solvent. The organic solvent can include one or more of methanol, ethanol, propanol, isopropanol, butanol, acetic acid, acetonitrile, acetone, and tetrahydrofuran.

In some embodiments, the crystallization can be performed without drying the precipitated cis,trans-muconic acid after recovery from the fermentation broth. In certain embodiments, the crystallization includes removing an undesired salt from the separated cis,trans-muconic acid. In various embodiments, the crystallization includes concentrating the crystallization medium after collecting a first crop of cis,trans-muconic acid and collecting a second crop of cis,trans-muconic from the concentrated medium.

In certain embodiments, the method for production of trans,trans-muconate comprises the production of cis,trans-muconate, isomerizing at least about 65% of the cis,trans-muconate to trans,trans-muconate, and isolating the trans,trans-muconate. The method can include isomerizing at least about 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the cis,trans-muconate to trans,trans-muconate. Alternatively, trans,trans-muconate can be produced or isomerized from cis,cis-muconate under suitable conditions (e.g., pH, temperature, catalyst, etc.).

In various embodiments, the isomerized reaction is catalyzed by $I_2$, by a precious metal hydrogenation catalyst, by a sponge metal hydrogenation catalyst, or by a skeletal hydrogenation catalyst. The precious metal can be any precious metal that functions as a hydrogenation catalyst (e.g., platinum, palladium, and the like). The sponge metal or skeletal catalyst can be a nickel-aluminum alloy (e.g., a RANEY® nickel catalyst available from W. R. Grace and Company). The metal catalysts can be in the form of a heterogeneous catalyst (e.g., particles) or a supported catalyst (e.g., on a support such as silica, alumina, carbon, and the like).

In some embodiments, providing cis,cis-muconate produced from a renewable carbon source through biocatalytic conversion employs a bacterial cell transformed with heterologous structural genes from *Klebsiella pneumoniae*, which express the enzymes 3-dehydroshikimate dehydratase and protocatechuate decarboxylase, and from *Acinetobacter calcoaceticus*, which expresses the enzyme catechol 1,2-dioxygenase, wherein a culture of the bacterial cell biocatalytically converts glucose to cis,cis-muconic acid at a rate at least sufficient to convert 1.38 M glucose to at least about 0.42 M cis,cis-muconic acid within about 88 hours. The bacterial cell transformant can include heterologous DNA sequences which express the enzymes 3-deoxy-D-arabino-heptulosonate 7-phosphate synthase and 3-dehydroquinate synthase. The bacterial cell transformant can includes heterologous DNA sequences which express the enzymes transketolase, 3-deoxy-D-arabino-heptulosonate 7-phosphate synthase and 3-dehydroquinate synthase. The bacterial cell can be selected from mutant cell lines having mutations in the common pathway of aromatic amino acid biosynthesis that block conversion of 3-dehydroshikimate to chorismate. The bacterial cell is selected from mutant cell lines having mutations in the common pathway of aromatic amino acid biosynthesis that block conversion of 3-dehydroshikimate to chorismate.

In certain embodiments, providing cis,cis-muconate produced from a renewable carbon source through biocatalytic conversion includes culturing a bacterial cell transformed with structural genes from *Klebsiella pneumoniae* which express the enzyme species 3-dehydroshikimate dehydratase and protocatechuate decarboxylase, and a structural gene from *Acinetobacter calcoaceticus* which expresses the enzyme species catechol 1,2-dioxygenase, in a medium containing a carbon source which is converted to 3-dehydroshikimate by the enzymes in the common pathway of aromatic amino acid biosynthesis of the cell, to produce cis,cis-muconic acid at a rate of at least about 0.95 millimoles/liter/hour, by the biocatalytic conversion of 3-dehydroshikimate. In other embodiments, cis,cis-muconic acid is produced at a rate of at least about 0.97, 1.0, 1.2, 1.4, 1.6, 1.8, 2.0 millimoles/liter/hour or greater.

In various embodiments, providing cis,cis-muconate produced from a renewable carbon source through biocatalytic conversion comprises culturing a transformed bacterial cell, which expresses heterologous structural genes encoding 3-dehydroshikimate dehydratase, protocatechuate decarboxylase, catechol 1,2-dioxygenase, transketolase, 3-deoxy-D-arabino-heptulosonate 7-phosphate synthase, and 3-dehydroquinate synthase, in a medium containing a carbon source which is converted to 3-dehydroshikimate, by the enzymes in the common pathway of aromatic amino acid biosynthesis of the cell, to produce cis,cis-muconic acid at a rate of at least about 0.95 millimoles/liter/hour by the biocatalytic conversion of 3-dehydroshikimate. In other embodiments, cis,cis-muconic acid is produced at a rate of at least about 0.97, 1.0, 1.2, 1.4, 1.6, 1.8, 2.0 millimoles/liter/hour or greater.

In some embodiments, providing cis,cis-muconate produced from a renewable carbon source through biocatalytic conversion comprises culturing a bacterial cell, transformed with structural genes from *Klebsiella pneumoniae* which express the enzyme species 3-dehydroshikimate dehydratase and protocatechuate decarboxylase and a structural gene from *Acinetobacter calcoaceticus* which expresses the enzyme catechol 1,2-dioxygenase in a medium containing a carbon source, under conditions in which the carbon source is biocatalytically converted to cis,cis-muconic acid at a rate of at least about 0.95 millimoles/liter/hour. In other embodiments, cis,cis-muconic acid is produced at a rate of at least about 0.97, 1.0, 1.2, 1.4, 1.6, 1.8, 2.0 millimoles/liter/hour or greater.

Other aspects and advantages of the invention will become apparent from the following drawings and description, all of which illustrate principles of the invention, by way of example only.

BRIEF DESCRIPTION OF THE DRAWINGS

The advantages of the invention described above, together with further advantages, can be better understood by referring to the following description taken in conjunction with the accompanying drawings. The drawings are not necessarily to scale, emphasis instead generally being placed upon illustrating the principles of the invention.

DETAILED DESCRIPTION OF THE INVENTION

The invention includes methods for producing cis,trans-muconic acid and trans,trans-muconic acid from fermentable carbon sources capable of being used by a host cell having a common pathway of aromatic amino acid biosynthesis, for example, one which is functional through to the intermediate DHS, plus the ability to express the enzymes aroZ, aroY, and catA. In one preferred embodiment, the method comprises the steps of culturing the host cell in the presence of a fermentable carbon source to produce cis,cis-muconic acid, and isomerizing the cis,cis-muconic acid to produce cis,trans-muconic acid or trans,trans-muconic acid.

Fermentable carbon sources can include essentially any carbon source capable of being biocatalytically converted into D-erythrose 4-phosphate (E4P) and phosphoenolpyruvate (PEP), two precursor compounds to the common pathway of aromatic amino acid biosynthesis. Suitable carbon sources include, but are not limited to, biomass-derived, or renewable, sources such as starches, cellulose, and sugar moieties such as glucose, pentoses, and fructose, as well as other carbon sources capable of supporting microbial metabolism, for example, carbon monoxide. In one embodiment, D-glucose can be used as the biomass-derived carbon source.

Host cells suitable for use in the present invention include members of genera that can be utilized for biosynthetic production of desired aromatic compounds. In some embodiments, such host cells are suitable for industrial-scale biosynthetic production of desired aromatic compounds. In particular, suitable host cells can have an endogenous common pathway of aromatic amino acid biosynthesis that is functional at least to the production of DHS. Common aromatic pathways are endogenous in a wide variety of microorganisms, and can be used for the production of various aromatic compounds. For example, microbial aromatic amino acid biosynthesis pathways as described in U.S. Pat. Nos. 5,168,056 and 5,616,496, the disclosures of both of which are incorporated herein by reference in their entirety, can be utilized in the present invention.

Figure 1:
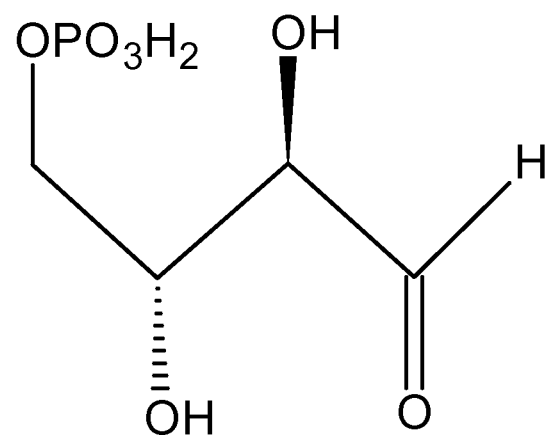
FIG. 1 shows the common pathway of aromatic amino acid biosynthesis and the divergent pathway synthesizing cis,cis-muconic acid from 3-dehydroshikimate.
Figure 1:
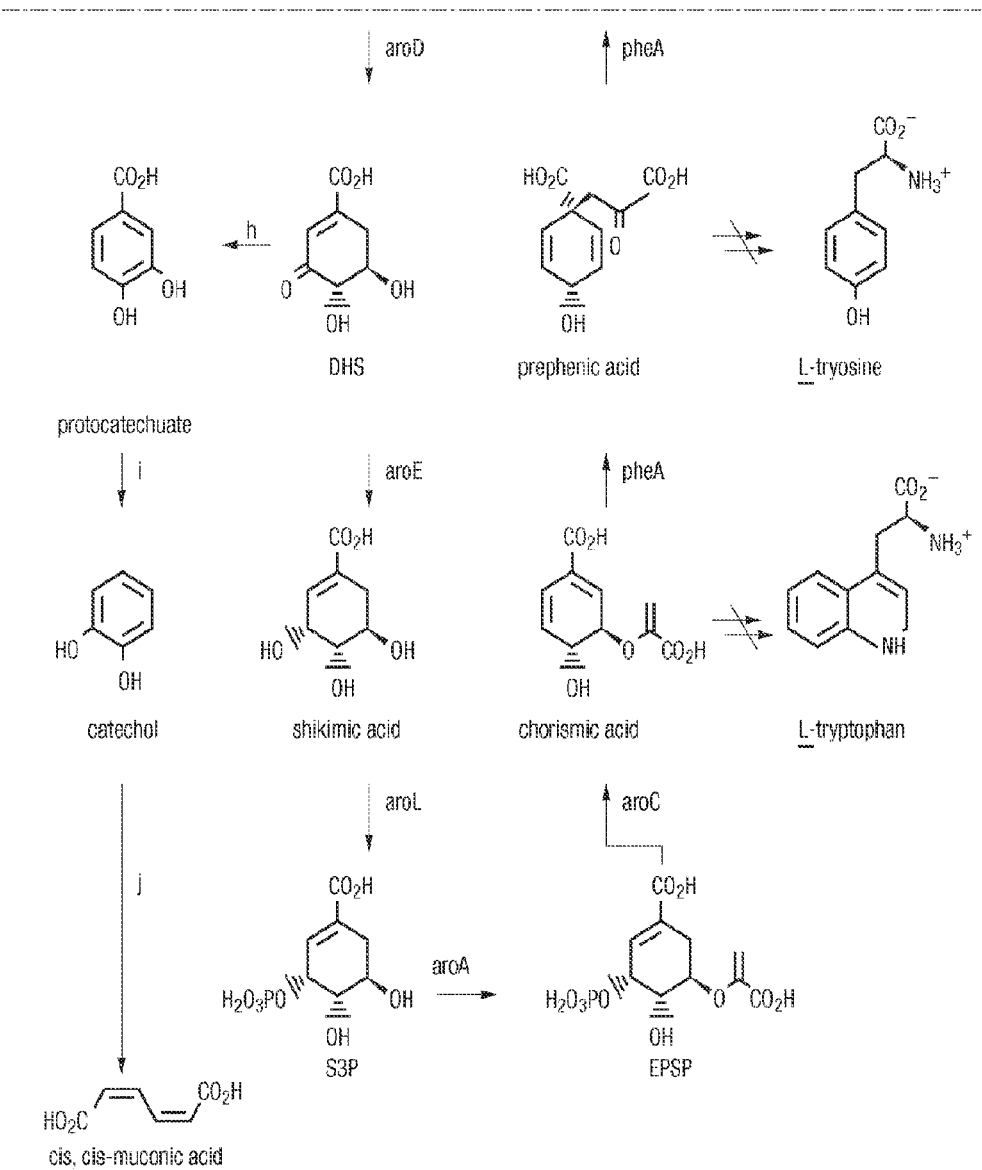

FIG. 1 shows the common pathway of aromatic amino acid biosynthesis and the divergent pathway synthesizing cis,cis-muconic acid from 3-dehydroshikimate through the common aromatic pathway that leads from E4P and PEP to chorismic acid with many intermediates in the pathway. The availability of E4P can be increased by the pentose phosphate pathway enzyme transketolase, encoded by the tkt gene. The intermediates in the pathway include 3-deoxy-D-arabino-heptulosonic acid 7-phosphate (DAHP), 3-dehydroquinate (DHQ), 3-dehydroshikimate (DHS), shikimic acid, shikimate 3-phosphate (S3P), and 5-enolpyruvoylshikimate-3-phosphate (EPSP). The enzymes in the common pathway include DAHP synthase (aroF), DHQ synthase (aroB), DHQ dehydratase (aroD), shikimate dehydrogenase (aroE), shikimate kinase (aroL, aroK), EPSP synthase (aroA) and chorismate synthase (aroC).

Host cells including common pathways of this type include prokaryotes belonging to the genera *Escherichia, Klebsiella, Corynebacterium, Brevibacterium, Arthrobacter, Bacillus, Pseudomonas, Streptomyces, Staphylococcus,* and *Serratia.* Eukaryotic host cells can also be utilized, for example, with yeasts of the genus *Saccharomyces* or *Schizosaccharomyces.*

More specifically, prokaryotic host cells can be derived from species that include *Escherichia coli, Klebsiella pneumonia, Corynebacterium glutamicum, Corynebacterium herculis, Brevibacterium divaricatum, Brevibacterium lactofermentum, Brevibacterium flavum, Bacillus brevis, Bacillus cereus, Bacillus circulans, Bacillus coagulans, Bacillus lichenformis, Bacillus megaterium, Bacillus mesentericus, Bacillus pumilis, Bacillus subtilis, Pseudomonas aeruginosa, Pseudomonas angulata, Pseudomonas fluorescens, Pseudomonas tabaci, Streptomyces aureofaciens, Streptomyces avermitilis, Streptomyces coelicolor, Streptomyces griseus, Streptomyces kasugensis, Streptomyces lavendulae, Streptomyces lipmanii, Streptomyces lividans, Staphylococcus epidermis, Staphylococcus saprophyticus,* and *Serratia marcescens.* Examples of eukaryotic host cells include *Saccharomyces cerevisiae* and *Saccharomyces carlsbergensis.*

Host cells can include auxotrophic mutant cell lines having a mutation that blocks the conversion of DHS to the branch point molecule, chorismate. Such mutants are unable to catalyze the conversion of 3-dehydroshikimate (DHS) into chorismate due to a mutation in one or more of the genes encoding shikimate dehydrogenase, shikimate kinase, EPSP synthase and chorismate synthase, and will thus accumulate elevated intracellular levels of DHS. Examples of such mutant cell lines include *Escherichia coli* strains AB2834, AB2829 and AB2849.

*E. coli* AB2834 is unable to catalyze the conversion of 3-dehydroshikimate (DHS) into shikimic acid due to a mutation in the aroE locus which encodes shikimate dehydrogenase. Use of *E. coli* AB2834 can ensure that the carbon flow directed into aromatic amino acid biosynthesis is not processed beyond DHS. Similarly *E. coli* AB2829 (which is unable to catalyze the conversion of shikimate 3-phosphate (S3P) into 5-enoipyruvylshikimate-3-phosphate (EPSP) due to a mutation in the aroA locus which encodes EPSP synthase) and *E. coli* AB2849 (which is unable to catalyze the conversion of EPSP into chorismic acid due to a mutation in the aroC locus which encodes chorismate synthase) also result in increased intracellular levels of DHS.

Host cells can be transformed so that the intracellular DHS can be used as a substrate for biocatalytic conversion to catechol, which can thereafter be converted to muconic acid. For example, host cells can be transformed with recombinant DNA to force carbon flow away from the common pathway of aromatic amino acid biosynthesis after DHS is produced and into a divergent pathway to produce muconic acid.

As shown in FIG. 1, the intermediates in the divergent pathway are protocatechuate, catechol, and cis,cis-muconic acid. The enzyme responsible for the biocatalytic conversion of DHS to protocatechuate is the enzyme 3-dehydroshikimate dehydratase, labeled "aroZ" in FIG. 1. The enzyme responsible for the decarboxylation of protocatechuate to form catechol is protocatechuate decarboxylase, labeled "aroY" in FIG. 1. Lastly, the enzyme catalyzing the oxidation of catechol to produce cis,cis-muconic acid is catechol 1,2-dioxygenase, labeled "catA" in FIG. 1. In accordance with standard notation, the genes for the expression of these enzymes are denoted using italics and are thus aroZ, aroY, and catA respectively. The cis,cis-muconic acid can subsequently be isomerized (not shown). In one embodiment of the invention, host cells may exhibit constitutive expression of the genes aroZ, aroY, and catA. In another embodiment, host cells may exhibit constitutive expression of any one or more of the genes aroZ, aroY and catA; or any combination of two thereof. In yet another embodiment, host cells may exhibit constitutive expression of none of aroZ, aroY and catA.

The enzymes 3-dehydroshikimate dehydratase and protocatechuate decarboxylase are recruited from the ortho cleavage pathways which enable microbes such as *Neurospora, Aspergillus, Acinetobacter, Klebsiella,* and *Pseudomonas* to use aromatics (benzoate and p-hydroxybenzoate) as well as hydroaromatics (shikimate and quinate) as sole sources of carbon for growth. DHS dehydratase plays a critical role in microbial catabolism of quinic and shikimic acid. Protocatechuate decarboxylase was formulated by Patel to catalyze the conversion of protocatechuate into catechol during catabolism of p-hydroxybenzoate by *Klebsiella aerogenes*. Reexamination of Patel's strain (now referred to as *Enterobacter aerogenes*) [(a) Grant, D. J. W.; Patel, J. C. Antonie van Leewenhoek 1969, 35, 325. (b) Grant, D. J. W. Antonie van Leewenhoek 1970, 36, 161] recently led Ornston to conclude that protocatechuate decarboxylase was not metabolically significant in catabolism of p-hydroxybenzoate [Doten, R. C.; Ornston, N. J. Bacteriol. 1987, 169, 5827].

A mechanism for transforming the host cell to direct carbon flow into the divergent pathway can involve the insertion of genetic elements including expressible sequences coding for 3-dehydroshikimate dehydratase, protocatechuate decarboxylase, and catechol 1,2-dioxygenase. Regardless of the exact mechanism utilized, it is contemplated that the expression of these enzymatic activities will be effected or mediated by the transfer of recombinant genetic elements into the host cell. Genetic elements as herein defined include nucleic acids (generally DNA and RNA) having expressible coding sequences for products such as proteins, apoproteins, or antisense RNA, which can perform or control pathway enzymatic functions. The expressed products can function as enzymes, repress or derepress enzyme activity, or control expression of enzymes. The nucleic acids coding these expressible sequences can be either chromosomal (e.g., inserted or integrated into a host cell chromosome) or extrachromosomal (e.g., carried by plasmids, cosmids, etc.).

The genetic elements of the present invention can be introduced into a host cell by plasmids, cosmids, phages, yeast artificial chromosomes or other vectors that mediate transfer of the genetic elements into a host cell. These vectors can include an origin of replication along with cis-acting control elements that control replication of the vector and the genetic elements carried by the vector. Selectable markers can be present on the vector to aid in the identification of host cells into which the genetic elements have been introduced. For example, selectable markers can be genes that confer resistance to particular antibiotics such as tetracycline, ampicillin, chloramphenicol, kanamycin, or neomycin.

Introducing genetic elements into a host cell can utilize an extrachromosomal multi-copy plasmid vector into which genetic elements are inserted. Plasmid borne introduction of the genetic element into host cells involves an initial cleaving of a plasmid with a restriction enzyme, followed by ligation of the plasmid and genetic elements in accordance with the invention. Upon recircularization of the ligated recombinant plasmid, transduction or other mechanism (e.g., electroporation, microinjection, and the like) for plasmid transfer is utilized to transfer the plasmid into the host cell. Plasmids suitable for insertion of genetic elements into the host cell include, but are not limited to, pBR322, and its derivatives such as pAT153, pXf3, pBR325, pBr327, pUC vectors, pACYC and its derivatives, pSC101 and its derivatives, and ColE1. In addition, cosmid vectors such as pLAFR3 are also suitable for the insertion of genetic elements into host cells. Examples of plasmid constructs include, but are not limited to, p2-47, pKD8.243A, pKD8.243B, and pSUaroZY157-27, which carry the aroZ and aroY loci isolated from *Klebsiella pneumoniae*, which respectively encode 3-dehydroshikimate dehydratase and protocatechuate decarboxylase. Additional examples of plasmid constructs include pKD8.292, which carries genetic fragments endogenous to *Acinetobacter calcoaceticus* catA, encoding catechol 1,2-dioxygenase.

Methods for transforming a host cell can also include insertion of genes encoding for enzymes, which increase commitment of carbon into the common pathway of aromatic amino acid biosynthesis. The expression of a gene is primarily directed by its own promoter, although other genetic elements including optional expression control sequences such as repressors, and enhancers can be included to control expression or derepression of coding sequences for proteins, apoproteins, or antisense RNA. In addition, recombinant DNA constructs can be generated whereby the gene's natural promoter is replaced with an alternative promoter to increase expression of the gene product. Promoters can be either constitutive or inducible. A constitutive promoter controls transcription of a gene at a constant rate during the life of a cell, whereas an inducible promoter's activity fluctuates as determined by the presence (or absence) of a specific inducer. For example, control sequences can be inserted into wild type host cells to promote overexpression of selected enzymes already encoded in the host cell genome, or alternatively can be used to control synthesis of extrachromosomally encoded enzymes.

Control sequences to promote overproduction of DHS can be used. As previously noted, DHS is synthesized in the common pathway by the sequential catalytic activities of the tyrosine-sensitive isozyme of 3-deoxy-D-arabinoheptulosonic acid 7-phosphate (DAHP) synthase (encoded by aroF) and 3-dehydroquinate (DHQ) synthase (encoded by aroB) along with the pentose phosphate pathway enzyme transketolase (encoded by tkt). The expression of these biosynthetic enzymes can be amplified to increase the conversion of D-glucose into DHS. Increasing the in vivo catalytic activity of DAHP synthase, the first enzyme of the common pathway, increases the flow of D-glucose equivalents directed into aromatic biosynthesis. However, levels of DAHP synthase catalytic activity are reached beyond which no further improvements are achieved in the percentage of D-glucose that is committed to aromatic biosynthesis. At this limiting level of aromatic amino acid biosynthesis, amplification of the catalytic levels of the pentose phosphate pathway enzyme transketolase achieves sizable increases in the percentage of D-glucose siphoned into the pathway.

Amplified transketolase activity can increase D-erythrose 4-phosphate concentrations. As one of the two substrates for DAHP synthase, limited D-erythrose 4-phosphate availability can limit DAHP synthase catalytic activity. Therefore, one method for amplifying the catalytic activities of DAHP synthase, DHQ synthase and DHQ dehydratase is to overexpress the enzyme species by transforming the microbial catalyst with a recombinant DNA sequence encoding these enzymes.

Amplified expression of DAHP synthase and transketolase can create a surge of carbon flow directed into the common pathway of aromatic amino acid biosynthesis, which is in excess of the normal carbon flow directed into this pathway. If the individual rates of conversion of substrate into product catalyzed by individual enzymes in the common aromatic amino acid pathway are less than the rate of DAHP synthesis, the substrates of these rate-limiting enzymes can accumulate intracellularly.

Microbial organisms such as *E. coli* frequently cope with accumulated substrates by exporting such substrates into the external environment, such as the bulk fermentation medium. This results in a loss of carbon flow through the common pathway since exported substrates are typically lost to the microbe's metabolism. DHQ synthase is an example of a rate-limiting common pathway enzyme. Amplified expression of DHQ synthase removes the rate-limiting character of this enzyme, and prevents the accumulation of DAHP and its nonphosphorylated analog, DAH. DHQ dehydratase is not rate-limiting. Therefore, amplified expression of aroF-encoded DAHP synthase, tkt-encoded transketolase and aroB-encoded DHQ synthase increases production of DHS, which in the presence of DHS dehydratase and protocatechuate decarboxylase is converted to catechol, which is subsequently biocatalytically converted to cis,cis-muconic acid, which can subsequently be isomerized.

One plasmid that can promote the efficiency of carbon flow along the common pathway between the carbon source and DHS is plasmid pKD136, which encodes the aroF, tkt and aroB genes. Plasmid pKD136-directs the surge of carbon flow into aromatic biosynthesis due to amplified expression of DAHP synthase (encoded by aroF) and transketolase (encoded by tkt). This surge of carbon flow is then delivered intact into DHS synthesis by pKD136 due to amplified expression of DHQ synthase (encoded by aroB).

Thus, as a preferred embodiment of the present invention, a heterologous strain of *Escherichia coli* expressing genes encoding DHS dehydratase, protocatechuate decarboxylase, and catechol 1,2-dioxygenase was constructed enabling the biocatalytic conversion of D-glucose to cis,cis-muconic acid. Efficient conversion of D-glucose to DHS was accomplished upon transformation of the host cell with pKD136. The strain *E. coli* AB2834/pKD136 was then transformed with plasmids pKD8.243A and pKD8.292. The result was *E. coli* AB2834/pKD136/pKD8.243A/pKD8.292 that expresses the enzymes 3-dehydroshikimate dehydratase (aroZ), protocatechuate decarboxylase (aroY) and catechol 1,2-dioxygenase (catA). This bacterial cell line was deposited with the American Type Culture Collection, 12301 Parklawn Drive, Rockville Md. 20852, on Aug. 1, 1995 and assigned accession number 69875.

In another embodiment, *E. coli* AB2834/pKD136 is transformed with plasmids p2-47 and pKD8.292 to generate *E. coli* AB2834/pKD136/p2-47/pKD8.292. In another embodiment, *E. coli* AB2834/pKD136 is transformed with plasmids pKD8.243B and pKD8.292 to generate *E. coli* AB2834/pKD136/p2-47/pKD8.292. Each of these heterologous host cell lines catalyzes the conversion of D-glucose into cis,cis-muconic acid. Synthesized cis,cis-muconic acid accumulates extracellularly and can be separated from the cells. Subsequently, the cis,cis-muconic acid can be isomerized into cis,trans-muconic acid and further to trans,trans-muconic acid as desired.

The present invention thus relates to a transformant of a host cell having an endogenous common pathway of aromatic amino acid biosynthesis. The transformant is characterized by the constitutive expression of heterologous genes encoding 3-dehydroshikimate dehydratase, protocatechuate decarboxylase, and catechol 1,2-dioxygenase. In one embodiment, the cell transformant is further transformed with expressible recombinant DNA sequences encoding the enzymes transketolase, DAHP synthase, and DHQ synthase. In another embodiment, the host cell is selected from the group of mutant cell lines including mutations having a mutation in the common pathway of amino acid biosynthesis that blocks the conversion of 3-dehydroshikimate to chorismate. In yet another embodiment, the genes encoding 3-dehydroshikimate dehydratase and protocatechuate decarboxylase are endogenous to Klebsiella pneumoniae. In a further embodiment, the heterologous genes encoding catechol 1,2-dioxygenase are endogenous to Acinetobacter calcoaceticus.

Renewable Muconate

Muconic acids produced from renewable, biologically derived carbon sources will be composed of carbon from atmospheric carbon dioxide which has been incorporated by plants (e.g., from a carbon source such as glucose, sucrose, glycerin, or plant oils). Therefore, such muconic acids include renewable carbon rather than fossil fuel-based or petroleum-based carbon in their molecular structure. Accordingly, the biosynthetic muconate that is the subject of this patent, and associated derivative products, will have a smaller carbon footprint than muconate and associated products produced by conventional methods because they do not deplete fossil fuel or petroleum reserves and because they do not increase the amount of carbon in the carbon cycle (e.g., life cycle analysis shows no net carbon increase to the global carbon balance).

The biosynthetic muconate and associated products can be distinguished from muconate and associated products produced from a fossil fuel or petrochemical carbon source by methods known in the art, such as dual carbon-isotopic finger printing. This method can distinguish otherwise chemically-identical materials, and distinguishes carbon atoms in the material by source, that is biological versus non-biological, using the $^{14}C$ and $^{13}C$ isotope ratios. The carbon isotope $^{14}C$ is unstable, and has a half life of 5730 years. Measuring the relative abundance of the unstable $^{14}C$ isotope relative to the stable $^{13}C$ isotope allows one to distinguish specimen carbon between fossil (long dead) and biospheric (alive and thus renewable) feedstocks (See Currie, L. A. "Source Apportionment of Atmospheric Particles," Characterization of Environmental Particles, J. Buffle and H. P. van Leeuwen, Eds., 1 of Vol. I of the IUPAC Environmental Analytical Chemistry Series (Lewis Publishers, Inc) (1992) 3-74). The basic assumption in radiocarbon dating is that the constancy of $^{14}C$ concentration in the atmosphere leads to the constancy of $^{14}C$ in living organisms.

When dealing with an isolated sample, the age of a sample can be deduced approximately by the relationship $t=(-5730/0.693)\ln(A/A_o)$ where t=age, 5730 years is the half-life of the unstable $^{14}C$ isotope, and A and $A_o$ are the specific $^{14}C$ activity of the sample and of the modern standard, respectively (Hsieh, Y., Soil ScL Soc. Am J., 56, 460, (1992)). However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of ca. $1.2\times10^{-12}$, with an approximate relaxation half-life of 7-10 years. (This latter half-life must be distinguished from the isotopic half-life, that is, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of fraction of modern carbon ($f_M$). $f_M$ is defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). For the current living biosphere (plant material), $f_M \approx 1.1$.

The ratio of the stable carbon isotopes $^{13}C$ and $^{12}C$ provides a complementary route to source discrimination and apportionment. The $^{13}C/^{12}C$ ratio in a given biosourced material is a consequence of the $^{13}C/^{12}C$ ratio in atmospheric carbon dioxide at the time the carbon dioxide is fixed and also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta^{13}C$ values. Furthermore, lipid matter of $C_3$ and $C_4$ plants analyze differently than materials derived from the carbohydrate components of the same plants as a consequence of the metabolic pathway. Within the precision of measurement, $^{13}C$ shows large variations due to isotopic fractionation effects, the most significant of which for the instant invention is the photosynthetic mechanism. The major cause of differences in the carbon isotope ratio in plants is closely associated with differences in the pathway of photosynthetic carbon metabolism in the plants, particularly the reaction occurring during the primary carboxylation (e.g., the initial fixation of atmospheric $CO_2$). Two large classes of vegetation are those that incorporate the $C_3$ (or Calvin-Benson) photosynthetic cycle and those that incorporate the $C_4$ (or Hatch-Slack) photosynthetic cycle. $C_3$ plants, such as hardwoods and conifers, are dominant in the temperate climate zones. In $C_3$ plants, the primary $CO_2$ fixation or carboxylation reaction involves the enzyme ribulose-1,5-diphosphate carboxylase and the first stable product is a 3-carbon compound. $C_4$ plants, on the other hand, include such plants as tropical grasses, corn and sugar cane. In $C_4$ plants, an additional carboxylation reaction involving another enzyme, phosphoenol-pyruvate carboxylase, is the primary carboxylation reaction. The first stable carbon compound is a 4-carbon acid, which is subsequently decarboxylated. The $CO_2$ thus released is refixed by the $C_3$ cycle.

Both $C_4$ and $C_3$ plants exhibit a range of $^{13}C/^{12}C$ isotopic ratios, but typical values are ca. −10 to −14 per mil ($C_4$) and −21 to −26 per mil ($C_3$) (Weber et al., J. Agric. Food Chem., 45, 2942 (1997)). Coal and petroleum fall generally in this latter range. The $^{13}C$ measurement scale was originally defined by a zero set by pee dee belemnite (PDB) limestone, where values are given in parts per thousand deviations from this material. The $\delta^{13}C$ values are in parts per thousand (per mil), abbreviated ‰, and are calculated as follows:

$$\delta^{13}C = (^{13}C/^{12}C)\text{sample} - (^{13}C/^{12}C)\text{standard}/(^{13}C/^{12}C)\text{standard} \times 1000\text{‰}$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45 and 46.

Therefore, the biosynthesized muconate and compositions including biosynthesized muconate can be distinguished from their fossil-fuel and petrochemical derived counterparts on the basis of $^{14}C$ ($f_M$) and dual carbon-isotopic fingerprinting, indicating new compositions of matter (e.g., U.S. Pat. Nos. 7,169,588, 7,531,593, and 6,428,767). The ability to distinguish these products is beneficial in tracking these materials in commerce. For example, products comprising both new and old carbon isotope profiles can be distinguished from products made only of old materials. Hence, the biosynthetic muconate and derivative materials can be followed in commerce on the basis of their unique profile.

EXAMPLES

Example 1

Cloning of the aroZ Gene

The gene encoding DHS dehydratase, designated aroZ, was isolated from a genomic library of *Klebsiella pneumoniae* DNA. Genomic DNA was purified from *K. pneumoniae* strain A170-40 and partially digested with BamH I to produce fragments in the range of 15 kb to 30 kb. The resulting DNA fragments were ligated to cosmid pLAFR3 which had previously been digested with BamH I and subsequently treated with calf intestinal alkaline phosphatase. pLAFR3 is a tetracycline resistant cosmid possessing the RK2 replicon. Ligated DNA was packaged using Packagene Packaging System (Promega), and the resulting phage particles were used to infect *E. coli* DH5α/pKD136. Plasmid pKD136 is a pBR325-based vector (pMB1 origin of replication) containing genes which encode transketolase (tkt), DAHP synthase (aroF), and DHQ synthase (aroB) as well as an ampicillin resistance gene. Colonies which were resistant to both tetracycline and ampicillin were subsequently plated onto chromogenic minimal medium (M9) plates containing D-glucose (4 g L), shikimic acid (0.04 g L), ferric citrate (0.07 g L), p-toluidine (1.9 g L), ampicillin (0.05 g L), and tetracycline (0.013 g L). After incubation at 37° C. for 48 h, the growth medium surrounding colony 5-87 appeared brown in color, analogous to the darkening of the medium that occurred when protocatechuic acid was spotted onto the plate. DNA was purified from a culture of colony 5-87 and consisted of pKD136 and a tetracycline resistant cosmid referred to as p5-87. Cosmid p5-87 contained a 14 kb BamH I fragment which when digested to completion with BamH I produced four detectable fragments of DNA.

Example 2

Confirmation of the Cloning of the aroZ Gene

Confirmation that cosmid p5-87 contained the aroZ gene relied on the fact that transformation of an *E. coli* strain which typically converts D-glucose into DHS could further convert DHS into protocatechuic acid. *E. coli* AB2834 accumulates DHS in the culture supernatant due to a mutation in the aroE gene, which encodes shikimate dehydrogenase. Conversion of D-glucose to DHS is maximized when AB2834 is transformed with pKD136. AB2834 was co-transformed with pKD136 and p5-87 to produce colonies that were resistant to both ampicillin and tetracycline. One liter of LB medium (4 L Erlenmeyer flask) was inoculated with an overnight culture (5 mL) of AB2834/pKD136/p5-87. The culture was grown at 37° C. for 8 h with agitation (250 rpm). The cells were then harvested and resuspended in one liter (4 L Erlenmeyer flask) of minimal M9 medium containing glucose (10 g L), shikimic acid (0.04 g L), ampicillin (0.05 g L), and tetracycline (0.013 g L). The culture was returned to 37° C. incubation. Aliquots of the culture were removed after 24 h and 64 h and centrifuged to remove cells. Five milliliters of isolated supernatant was collected from each sample and the water was removed in vacuo. Samples were redissolved in $D_2O$ and concentrated in vacuo. Repetition of this procedure resulted in exchange of residual water with $D_2O$ and samples suitable for analysis by $^1H$ NMR. Using the sodium salt of 3-(trimethylsilyl)ProPionic-2,2,3,3-$d_4$ acid as an internal standard, it was determined that approximately 9 mM protocatechuic acid had accumulated in the culture supernatant. Diagnostic resonances at δ6.94 (d, 7 Hz, 1H) and δ 7.48 (d, 7 Hz, 2H) were indicative of protocatechuic acid. DHS was not detected in the culture supernatant. It was concluded from this experiment that the gene encoding DHS dehydratase (aroZ) was localized on plasmid p5-87.

Example 3

Subcloning of the aroZ Gene

In an effort to minimize the size of the aroZ-encoding insert plasmid p5-87 was digested with BamH I and the resulting fragments were ligated to vector pSU19 which had previously been digested with BamH I and treated with phosphatase. Plasmid pSU19 contains the p15A replicon and the gene which imparts resistance to chloramphenicol. Following transformation of the ligation products into *E. coli* DH5α/pKD136, the resulting ampicillin and chloramphenicol resistant colonies were screened as described in Example 1 for the ability to turn chromogenic minimal medium agarose plates containing p-toluidine and ferric citrate brown. Using this technique, plasmid pSU1-31 was isolated which consisted of a 3.5 kb BamH I insert contained in pSU19. When AB2834/pKD136/pSU1-31 was grown on a 1 L scale under conditions similar to those described in Example 1, $^1H$ NMR analysis of the culture supernatant of indicated that 11 mM protocatechuic acid accumulated extracellularly.

Example 4

Cloning of the aroY Gene

A fragment of DNA containing the aroY gene was isolated based on the fact that a strain which normally synthesizes protocatechuate will instead synthesize catechol in the presence of catalytically active protocatechuate decarboxylase. Cosmid p4-20 was prepared which contained the 3.5 kb BamH I aroZ fragment localized in pLAFR3. A library of *Klebsiella pneumoniae* DNA digested with EcoR I was prepared in cosmid p4-20 analogous to what had been constructed earlier in pLAFR3. DNA packaged in lambda phage heads was used to infect *E. coli* DH5α/pKD136, resulting in colonies resistant to both ampicillin and tetracycline. Colonies were screened on chromogenic minimal medium agarose plates containing p-toluidine and ferric citrate. Since addition of catechol to chromogenic minimal medium gives rise to a more intense darkening of the surrounding agarose than the addition of an equal quantity of protocatechuic acid, it was expected that those colonies synthesizing catechol could be selected from a background of colonies synthesizing protocatechuate. After incubation at 37° C. for approximately 24 h, colony 2-47 was producing a local region of brown that was lacking from all other colonies.

Isolation of DNA from colony 2-47 yielded plasmid pKD136 and plasmid p2-47 which were subsequently co-transformed into competent cells to yield *E. coli* AB2834/pKD136/p2-47. The culture supernatant of AB2834/pKD136/p2-47 was analyzed by $^1H$ NMR as described in Example 2. After 48 h in minimal medium, a solution of 56 mM D-glucose was converted to a solution of 20 mM catechol by AB2834/pKD136/p2-47.

Example 5

Subcloning of the aroY Gene

Figure 2:
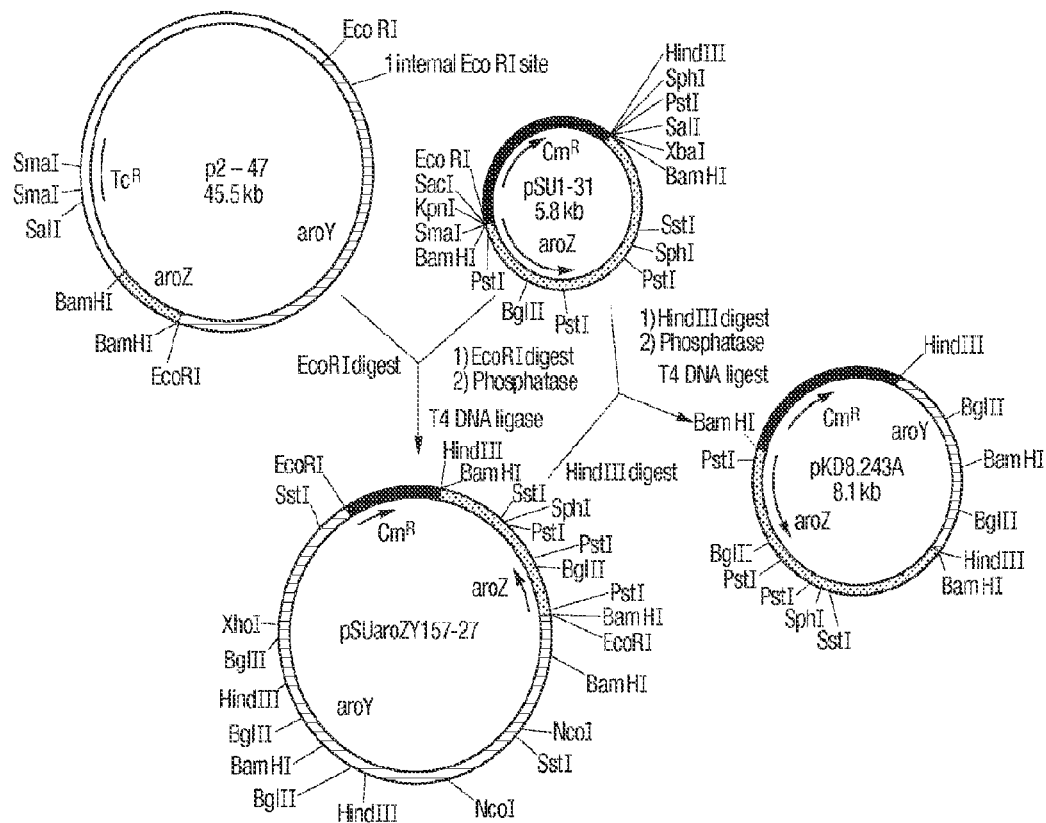
FIG. 2 shows a plasmid map of plasmid p2-47 and illustrates how plasmid pKD8.243A can be generated from plasmids p2-47, pSU1-31, and pSUaroZY 157-27.

Similar to the original strategy for isolation of the DNA encoding protocatechuate decarboxylase, subcloning of the aroY EcoR I fragment to its minimal size also relied on synthesis of catechol by an aroE host strain in the presence of DHS dehydratase. Digestion of p2-47 to completion with EcoR I indicated that the aroY insert consisted of two EcoR I fragments of approximately 8 kb and 11.9 kb. Localization of the 11.9 kb EcoR I fragment in pSU1-31 yielded plasmid pSUaroZY157-27. When grown on a 1 L scale under conditions similar to those described in Example 2, *E. coli* AB2834/pKD136/pSUaroZY157-27 accumulated 16 mM catechol in the culture supernatant when supplied with 56 mM D-glucose. Mapping of the 11.9 kb EcoR I fragment in conjunction with further subcloning indicated that the aroY gene was likely located near the middle of the 11.9 kb fragment. Digestion of pSUaroZY157-27 with Hind III produced a 2.3 kb Hind III fragment which was inserted into pSU1-31, yielding plasmid pKD8.243A (FIG. 2). Plasmid pKD8.243B in which the 2.3 kb Hind III fragment is in the opposite orientation relative to the vector was also isolated. Each of these plasmids was co-transformed into AB2834 with plasmid pKD136. When grown on a 1 L scale under conditions similar to those described in Example 2, AB2834/pKD136/pKD8.243A synthesized 16 mM catechol from 56 mM D-glucose within 48 h whereas AB2834/pKD136/pKD8.243B synthesized 10 mM catechol. Protocatechuic acid (<4 mM) was also detected in some of the culture supernatants, though not on a consistent basis and not always at the end of the microbial synthesis. Bacterial cell line AB2834/pKD136/pKD8.243A, which expresses the enzyme species 3-dehydroshikimate dehydratase and protocatechuate decarboxylase, was deposited with the American Type Culture Collection, 12301 Parklawn Drive, Rockville Md. 20852, on Mar. 19, 1996 was assigned accession number 98014.

Example 6

Figure 3:
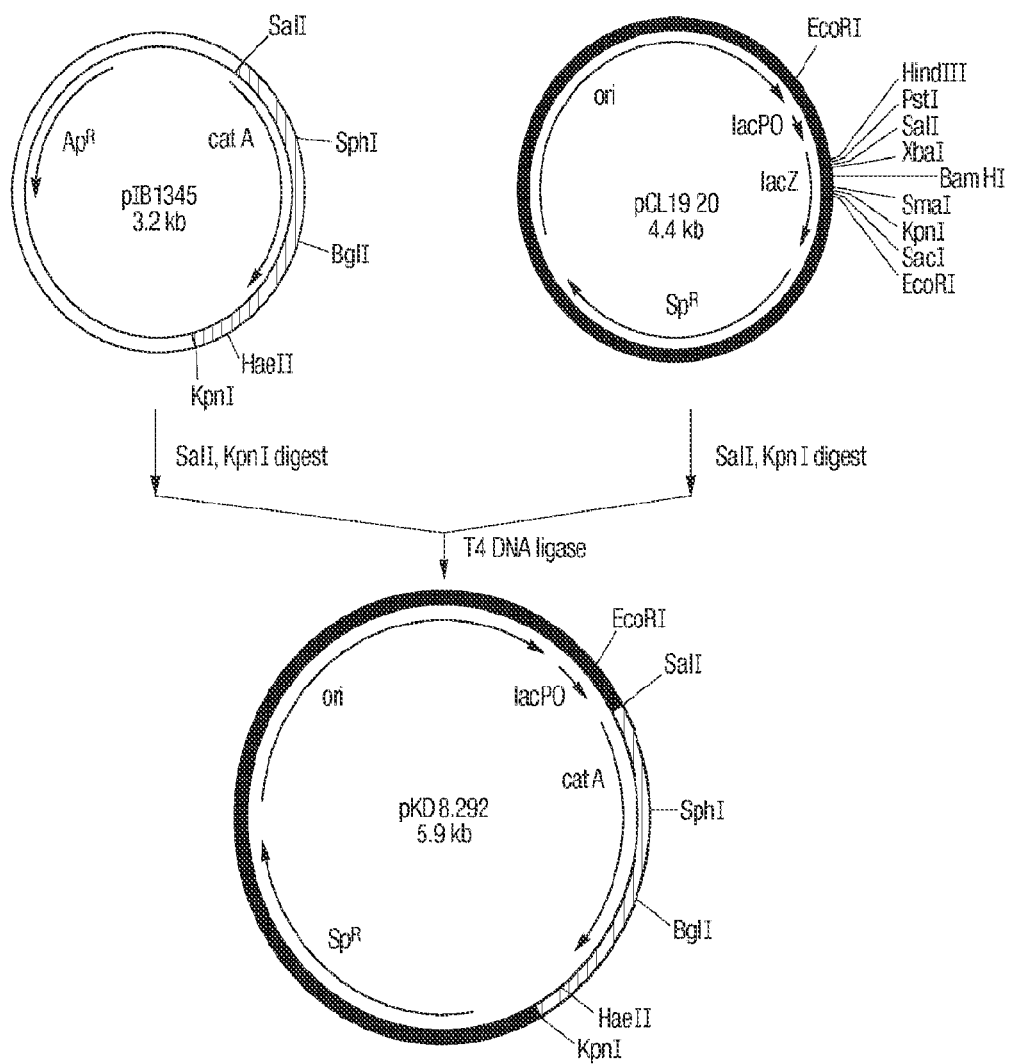
FIG. 3 shows a plasmid map of pKD8.292 and illustrates how plasmid pKD8.292 can be generated from plasmids pIB1345 and pCL1920.

Enzymatic Activities of DHS Dehydratase, Protocatechuate Decarboxylase, and Catechol 1,2-Dioxygenase Expression of catechol 1,2-dioxygenase in an organism capable of catalyzing conversion of D-glucose into catechol was expected to result in microbial synthesis of cis,cis-muconic acid. Plasmid pIB 1345 was obtained which contains the *Acinetobacter calcoaceticus* catA gene expressed from a lac promoter supplied by the host vector pUC19. A three plasmid system was designed for microbial synthesis of cis,cis-muconate from D-glucose. Plasmids pKD136 (pMB1 origin, ampicillin resistance) and pKD8.243A (p15A origin, chloramphenicol resistance) were found to be stably maintained under the growth conditions employed. A third plasmid, pCL1920, was chosen for expression of catechol 1,2-dioxygenase. Plasmid pCL1920 is a low copy vector containing the pSC101 origin of replication and a gene which confers resistance to spectinomycin. Digestion of pIB1345 with Sal I and Kpn I yielded a 1.5 kb fragment which was subsequently localized in pCL1920 to produce pKD8.292 (FIG. 3) in which catechol 1,2-dioxygenase was expressed from the vector-encoded lac promoter. Transformation of AB2834/pKD136 with pKD8.243A and pKD8.292 yielded colonies which were resistant to ampicillin, chloramphenicol, and spectinomycin.

Enzyme activities were determined to confirm that *E. coli* AB2834/pKD136/pKD8.243A/pKD8.292 was expressing each of the genes from the ortho cleavage pathway necessary to convert DHS into cis,cis-muconate. Cultures of AB2834/pKD136/pKD8.243A/pKD8.292 were grown in LB (1 L) containing IPTG (0.2 mM), ampicillin (0.05 g), chloramphenicol (0.02 g) and spectinomycin (0.05 g) for 10 h at 37° C., 250 rpm. Cells were harvested and resuspended in 100 mM Tris HCl, pH 7.5, 2.5 mM $MgCl_2$. After two passages through a French pressure cell (16,000 psi), the lysate was clarified by centrifugation (40000 g, 30 min, 4° C.). To measure DHS dehydratase activity, each assay contained (final volume of 1 mL) 100 mM Tris HCl, pH 7.5, 25 mM $MgCl_2$, mM DHS, and cellular lysate. After addition of DHS, formation of protocatechuate ($\epsilon$=3890 $M^1$ $cm^1$) was monitored at 290 nm for several minutes. DHS dehydratase activity measured for three samples of AB2834/pKD136/pKD8.243A/pKD8-292 was determined to be 0.078 units mg ±0.009, where one unit is the amount of enzyme necessary to convert 1 mmol of DHS to protocatechuic acid in 1 min.

Catechol 1,2-dioxygenase specific activity was determined using the same cellular lysate samples produced above. Each assay contained 100 mM potassium phosphate, pH 7.5, 0.2 mM catechol, and cellular lysate. Formation of cis,cis-muconate was monitored by following the increase in absorbance at 260 nm. Assuming a difference in molar extinction coefficient between cis,cis-muconate and catechol to be 16,000 $M^1$ $cm^1$ under the conditions of the assay, catechol 1,2-dioxygenase activity in AB2834/pKD136/pKD8.243A/PKD8-292 was determined to be 0.25 units mg ±0.03, where one unit corresponds to the formation of 1 μmol of cis,cis-muconate per min.

To determine the activity of protocatechuate decarboxylase, AB2834/pKD136/pKD8.243A/pKD8.292 was grown as described previously in Example 6. Cells were harvested and resuspended in 75 mM phosphate buffer, pH 7.1. Following disruption by passage through a French pressure cell (16000 psi), the lysate was clarified by centrifugation (40000 g, 30 min, 4° C.). Protocatechuate decarboxylase activity was determined by following the consumption of protocatechuic acid. Each assay (final volume of 1 mL) contained 75 mM sodium phosphate, pH 6.0, 0.3 mM protocatechuic acid, and cellular lysate. The loss of absorbance at 290 nm was monitored over time. Protocatechuate decarboxylase activity in AB2834/pKD136/pKD8.243A/pKD8.292 was determined to be 0.028 units mg ±0.009, where one unit corresponds to the oxidation of 1 mmol of protocatechuic acid per min.

Example 7

Conversion of D-Glucose to cis,cis-Muconate

Microbial synthesis of cis,cis-muconate from D-glucose utilizing *E. coli* AB2834/pKD136/pKD8.243A/pKD8.292 proceeded as follows. One liter of LB medium (in 4 L Erlenmeyer shake flask) containing IPTG (0.2 mM), ampicillin (0.05 g), chloramphenicol (0.02 g) and spectinomycin (0.05 g) was inoculated with 10 mL of an overnight culture of AB2834/pKD136/pKD8.243A/pKD8.292. Cells were grown at 250 rpm for 10 h at 37° C. The cells were harvested, resuspended in 1 L of M9 minimal medium containing 56 mM D-glucose, shikimic acid (0.04 g), IPTG (0.2 mM), ampicillin (0.05 g), chloramphenicol (0.02 g) and spectinomycin (0.05 g). The cultures were returned to 37° C. incubation. After resuspension in minimal medium the pH of the culture was closely monitored, particularly over the initial 12 h. When the culture reached a pH of 6.5, 5 N NaOH was added to adjust the pH back to approximately 6.8. Over the 48 h accumulation period, the culture was not allowed to fall below pH 6.3. After 24 h in minimal medium 12 mM cis,cis-muconate and 1 mM protocatechuate were detected, using methods described in Example 2, in the culture supernatant along with 23 mM D-glucose. After 48 h in minimal medium AB2834/pKD136/pKD8.243A/pKD8.292 had replaced the 56 mM D-glucose with 17 mM cis,cis-muconate.

Example 7A

Conversion of Glucose to cis,cis-Muconate at 20 L Scale

FIG. 7A shows the results of a 20 L batch cultivation of WN1/pWN2.248 for the production of cis,trans-muconic acid. The culture was induced at $OD_{600}$=33 using IPTG (100 mM, 10 mL) every 6 hours. After about 88 hours, the muconic acid titer was 59 g/L (a 30% yield) and the total amount of muconic acid synthesized was 1475 g. This corresponds to the conversion of about 1.38 M glucose to 0.42 M cis,trans-muconic acid in about 88 hours. Table 1 shows the cis,trans-muconic acid production rates at various times throughout the culture. (Note that the table shows the productivity post-induction as a function of time. If the outlying data points are excluded (48 h, after inoculation and 58 h, after inoculation) the average rate is 1.1 g/L/h.) It was also found that the recrystallization of IPTG (e.g., in ethyl acetate) can increase the muconic acid titer. For example, several experiments showed titers of about 55-60 g/L muconic acid on a 20 L scale, which is about a 17% increase over the about 50 g/L production observed without recrystallization of IPTG (e.g., a yield of about 30% versus 24%).

TABLE 1 cis,cis-muconate production rates in the fermentation.

| post-induction (h) | cis,cis-muconate (g/L) | rate (g/L/h) | rate (mmol/L/h) |
|---|---|---|---|
| 0 | 0.52 | | |
| 6 | 7.46 | 1.16 | 8.14 |
| 12 | 16.14 | 1.45 | 10.18 |
| 18 | 22.37 | 1.04 | 7.31 |
| 24 | 28.26 | 0.98 | 6.91 |
| 30 | 35.14 | 1.15 | 8.07 |
| 36 | 39.57 | 0.74 | 5.20 |
| 42 | 46.72 | 1.19 | 8.39 |
| 48 | 47.53 | 0.14 | 0.95 |
| 53 | 52.19 | 0.93 | 6.56 |
| 58 | 51.55 | −0.13 | −0.90 |
| 66.5 | 59.22 | 0.90 | 6.35 |

Following the production of cis,cis-muconate from glucose or other fermentable carbon source, methods for producing cis,trans-muconate include (i) providing cis,cis-muconate produced from a renewable carbon source through biocatalytic conversion; (ii) isomerizing cis,cis-muconate to cis,trans-muconate under reaction conditions in which substantially all of the cis,cis-muconate is isomerized to cis,trans-muconate; and (iii) separating the cis,trans-muconate and crystallizing the cis,trans-muconate.

The isomerization reaction can be catalyzed by an acid, for example, an inorganic acid. The isomerization reaction can be carried out in solution at a pH of below pH 7, and preferably at a pH of about 4 or lower. In some examples, the pH of the isomerization can be above the value at which one or more of cis,cis-muconate, cis,trans-muconate, and trans,trans-muconate precipitates out of solution.

The isomerization reaction can be carried out at a temperature greater than room temperature or greater than fermenter temperature. For example, the isomerization reaction can be carried out at a temperature of about 30° C. or greater, and preferably above 60° C. or greater.

The separating step can include precipitating the cis,trans-muconate from solution by acidifying the solution. Preferably, the solution can be acidified to a pH below about 3. The separating step can include cooling the solution. The solution can be cooled to a temperature below about 30° C., and preferably below 0° C.

Recrystallization can employ an organic solvent. The organic solvent can include one or more of a polar aprotic solvent (e.g., acetic acid, butanol, isopropanol, propanol, ethanol, methanol, formic acid, water), a polar protic solvent (e.g., dioxane, tetrahydrofuran, dichloromethane, acetone, acetonitrile, dimethlyformamide, dimethyl sulfoxide), and a non-polar solvent (e.g., hexane, benzene, toluene, diethyl either, chloroform, ethyl acetate).

In certain embodiments, the method includes removing a salt from the separated cis,trans-muconate. The salt can include an inorganic salt.

In certain embodiments, the method includes isomerizing at least about 50% of the cis,trans-muconate to trans,trans-muconate, and preferably more than 95%.

Figure 11:
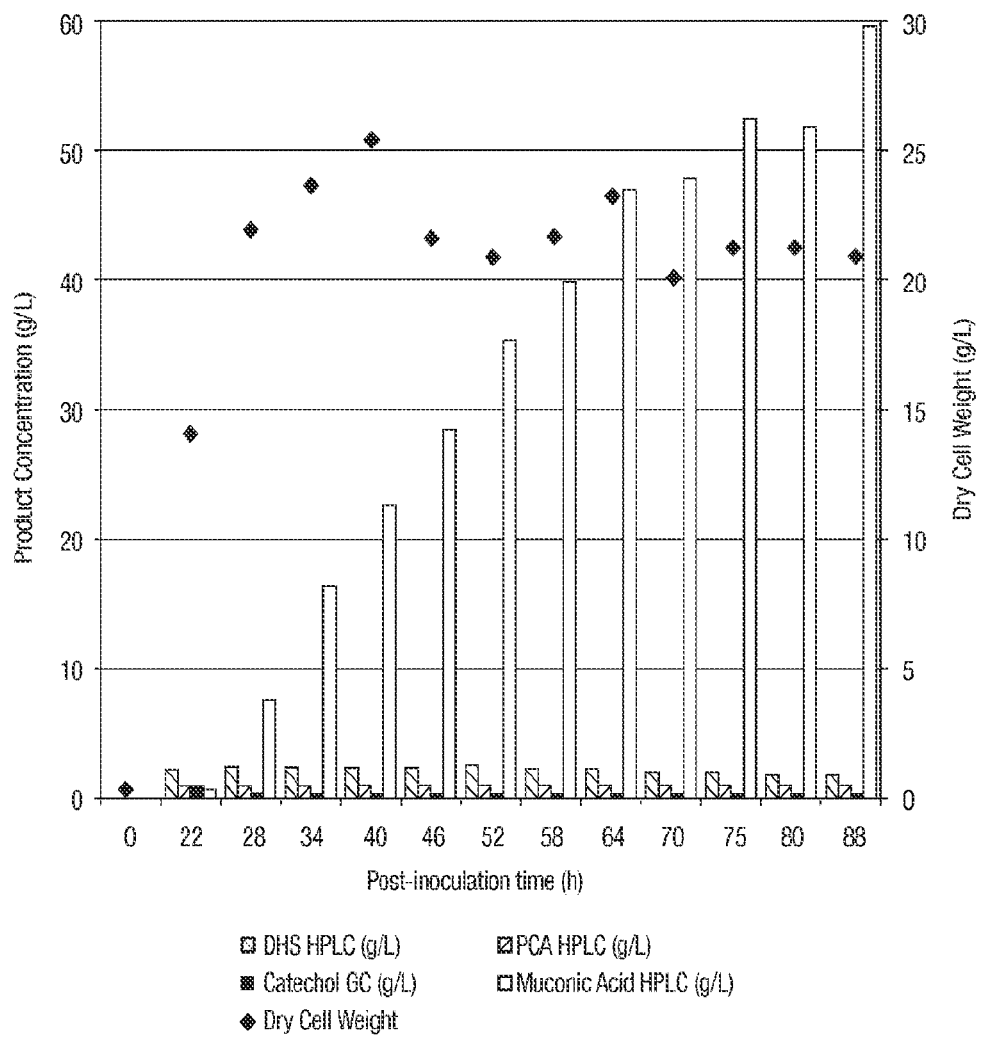
FIG. 11 shows a batch cultivation production of muconic acid.

FIG. 11 shows the results of a 20 L batch cultivation of WN1/pWN2.248 for the production of cis,trans-muconic acid induced at $OD_{600}$=33 using IPTG (100 mM, 10 mL) every 6 hours. After about 88 hours, the muconic acid titer was 59 g/L (a 30% yield) and the total amount of muconic acid synthesized was 1475 g, which corresponds to the conversion of about 1.38 M glucose to 0.42 M cis,trans-muconic acid in about 88 hours.

Example 8

In Situ Isomerization of cis,cis-Muconate to cis,trans-Muconate in a Fermenter cis,cis-muconate produced from a renewable carbon source through biocatalytic conversion (e.g., according to the method of Examples 7 and 7A) was provided, and the fermentation culture including the cis,cis-muconate was warmed to 60° C. The warmed fermentation culture was adjusted to pH 4 by adding 2 N sulfuric acid over 0.5 h. The acidified culture was allowed to react for 3.5 h.

The reaction was monitored by $^1$H NMR and HPLC equipped with the Prevail Organic Acid Column (150 mm×4.6 mm), to determine the endpoint of the reaction. These data are presented, along with control experiments at neutral pH, in FIGS. 7-10. In general, such isomerization reactions can be monitored to determine appropriate reaction parameters (e.g., time, temperature, pH, and the like).

Figure 5:
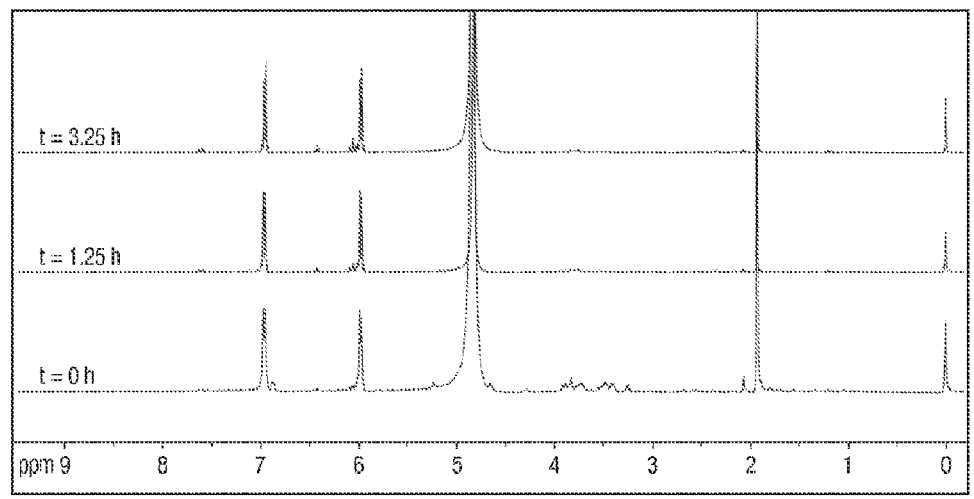
FIG. 5 shows examples of $^1$H NMR traces for a muconate isomerization reaction at pH 7.

FIG. 5 shows $^1$H NMR traces for a cis,cis- to cis,trans-muconate isomerization reaction at pH 7 in a crude fermentation broth. The time traces from 0 to 1.25 and 3.25 hours demonstrate that there is essentially no isomerization from cis,cis to cis,trans muconic acid at neutral pH (e.g., which is the approximate pH level during an actual fermentation). Thus, no or negligible isomerization of cis,cis-muconate occurs during an actual fermentation.

Figure 6:
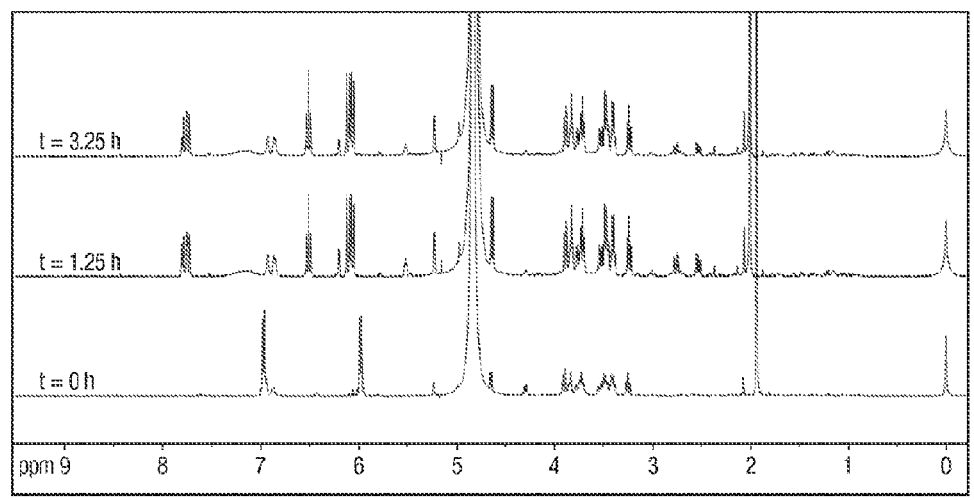
FIG. 6 shows examples of $^1$H NMR traces for a muconate isomerization reaction at pH 4.

FIG. 6 shows $^1$H NMR traces for a muconate isomerization reaction at pH 4 in a crude fermentation broth. The time traces from 0 to 1.25 and 3.25 hours demonstrate that isomerization from cis,cis to cis,trans-muconic acid proceeds rapidly at acidic pH, and that the isomerization is essentially complete after about 1.25 hours.

Figure 7:
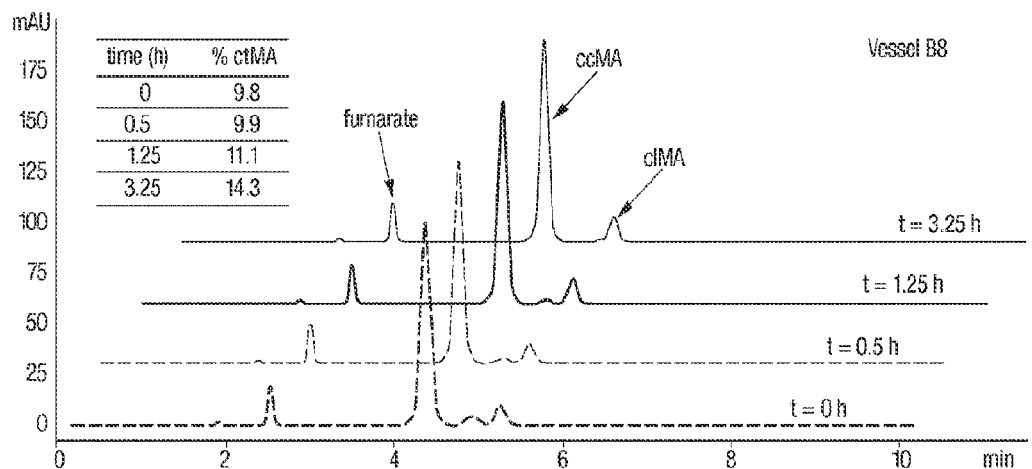
FIG. 7 shows examples of HPLC traces for a muconate isomerization reaction at pH 7.
Figure 9:
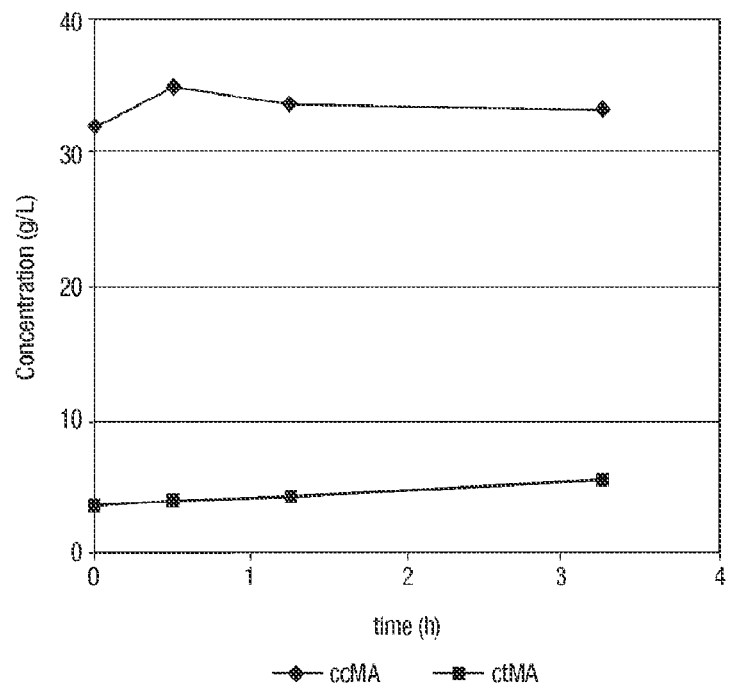
FIG. 9 shows examples of a time course for a muconate isomerization reaction at pH 7.

FIG. 7 shows HPLC traces for a muconate isomerization reaction at pH 7. FIG. 9 shows a time course for a muconate isomerization reaction at pH 7. As with the $^1$H NMR traces, these HPLC traces and time course demonstrate that there is essentially no isomerization from cis,cis to cis,trans-muconic acid at neutral pH.

Figure 8:
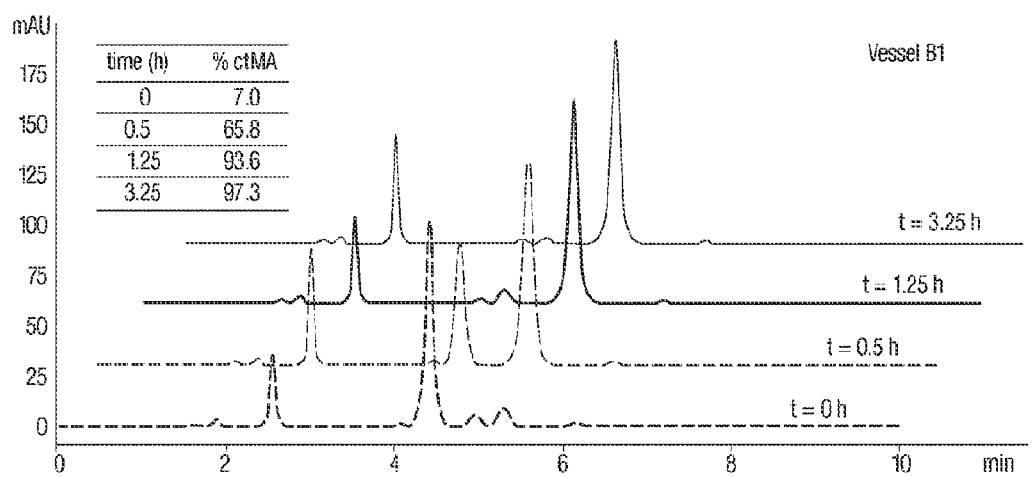
FIG. 8 shows examples of HPLC traces for a muconate isomerization reaction at pH 4.
Figure 10:
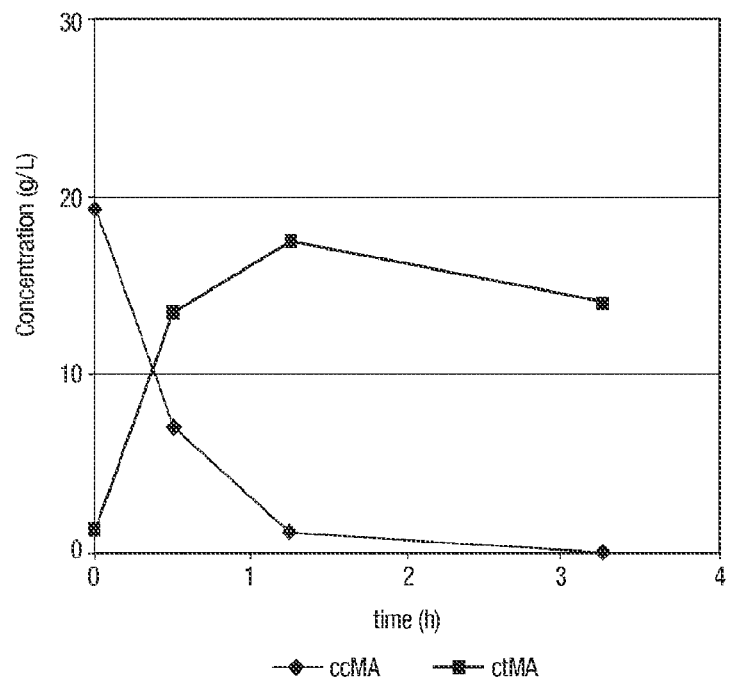
FIG. 10 shows examples of a time course for a muconate isomerization reaction at pH 4.

FIG. 8 shows HPLC traces for a muconate isomerization reaction at pH 4. FIG. 10 shows a time course for a muconate isomerization reaction at pH 4. As with the $^1$H NMR traces, these HPLC traces and time course demonstrate that that isomerization from cis,cis- to cis,trans-muconic acid proceeds rapidly at acidic pH, and that the isomerization is essentially complete after about 1.25 hours.

Example 9

Separation of cis,trans-Muconic Acid from Fermentation Broth by Acidification, Precipitation, and Filtration Following isomerization (e.g., as in Example 8), broth containing cis,trans-muconic acid was cooled to approximately ambient temperature and the cells, cell debris and precipitated solids were removed from the culture broth by centrifugation. Alternatively, such solids can be removed by filtration (e.g., through a 100 kD SARTOCON® Slice cassette). The cell-free broth was then clarified by filtration (e.g., through a 10 kD SARTOCON® Slice cassette), to remove proteins.

After filtration, the pH of the clarified broth was adjusted to pH 1.5 by adding concentrated sulfuric acid. The amount of cis,trans-muconate that precipitates at various pH values is shown in Table 2.

TABLE 2

The precipitation of cis,trans-muconate at different pH values.

| pH | ctMA in precipitate (weight %) | % ctMA in filtrate (weight %) | ctMA/total MA (HPLC %) |
|---|---|---|---|
| 4.7 | 0 | 100 | 98 |
| 4.0 | 22 | 75 | 94 |
| 3.5 | 58 | 26 | 86 |
| 3.0 | 61 | 22 | 83 |
| 2.5 | 64 | 18 | 87 |
| 2.0 |  | 18 | 86 |

The acidified broth was chilled to 4° C. for 1.5 h without agitation, during which time crude cis,trans-muconic acid precipitated as a slightly yellow solid. This material was recovered by filtration and comprised about 60% of the cis, trans-muconic acid present in the clarified broth. The precipitation can be allowed to continue for a longer period of time (e.g., overnight) and/or at a lower temperature (e.g., −20° C.), to increase product recovery while mitigating salt contamination.

The filtrate contained further cis,trans-muconic acid. In order to recover the further cis,trans-muconic acid, the filtrate was evaporated under reduced pressure, to reduce the volume by about 50%. The concentrated filtrate was chilled to −20° C. overnight, during which time a second crop of crude cis,trans-muconic acid precipitated. The precipitate was again recovered by filtration.

The crude cis,trans-muconic acid solids were combined and crystallized using acetonitrile to produce purified cis, trans-muconate as a white solid. Crystallization using methanol provided similar yields. Methanol also mitigated salt contamination in the purified product.

Figure 4A:
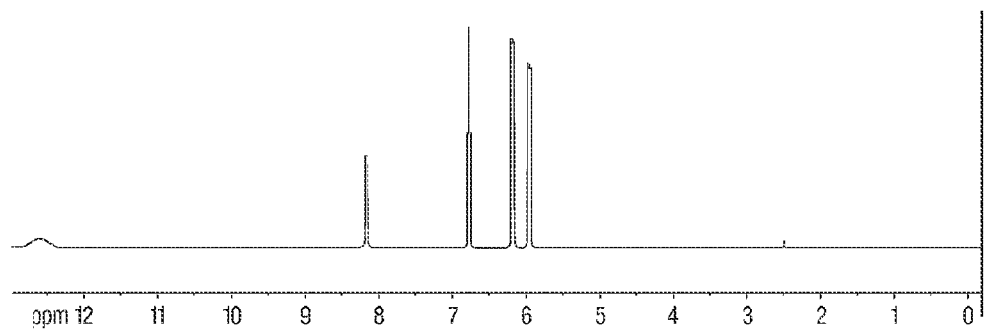
FIGS. 4A and 4B show examples of $^1$H NMR spectra of cis,trans-muconic acid in different media.
Figure 4B:
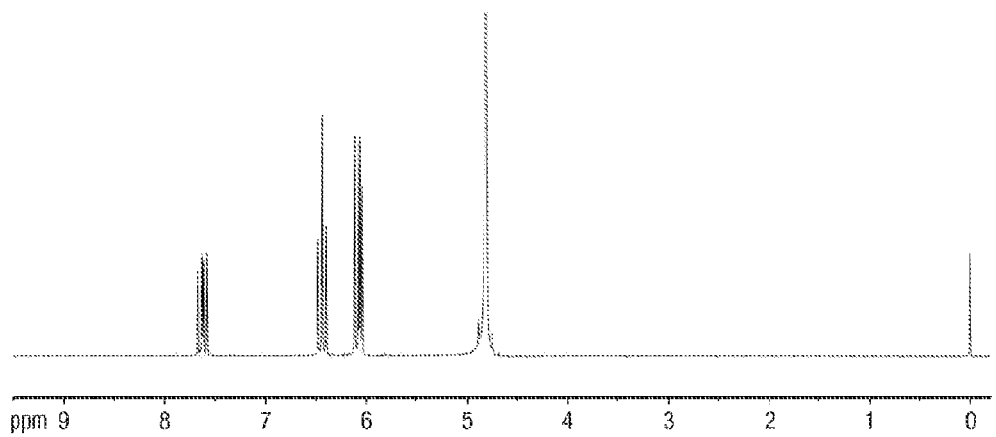

FIG. 4A shows an $^1$H NMR spectrum of crystallized cis, trans-muconic acid. FIG. 4B shows an $^1$H NMR spectrum of crystallized cis,trans-muconic, resuspended in a minimal salts medium lacking glucose. The FIG. 4B spectrum approximates the NMR spectral shifts in cis,trans-muconic acid caused by other components in the fermentation broth, and thus allows for comparisons monitoring the cis,cis to cis,trans isomerization reaction in the fermentation broth.

Example 10

Extraction of cis,trans-Muconic Acid from Fermentation Broth Using an Organic Solvent Advantageously, cis,trans-muconic acid is surprisingly and unexpectedly more soluble in organic solvents than either of the cis,cis or trans,trans isomers. Therefore, a separating step (e.g., the separating step of Example 8) can include extracting the cis,trans-muconate from solution (e.g., a fermentation broth) using an organic solvent.

The solution from which the cis,trans-muconate is extracted can be a whole culture fermentation broth or a cell free, protein free fermentation broth. Cells can be removed from a broth, for example, by filtration (e.g., passing the broth through a 0.1 µM hollow fiber filtration unit). Proteins can be removed from a broth, for example, by filtration (e.g., through a 10 kD tangential flow filtration system available, for example, from SARTOCON®).

The organic solvent for extraction (e.g., solvent that is immiscible with an aqueous phase) can include, for example, one or more of: methyl isobutylketone (MIBK), ethyl acetate, isopropyl acetate (propyl acetate), heptanes (mixture), methyl tert-butylether, xylenes, methylene chloride, cyclohexanol, decalin, tetralin, tetralone, cyclohexane, butyl acetate, methyl tetrahydrofuran (THF), cyclohexanone/cyclohexanol (commercial mixture), 1-octanol, isoamyl alcohol, and 2-ethylhexanol.

Other organic solvents which can be added to the aqueous phase and which will facilitate both the extraction and concurrent or subsequent esterification of the cis,trans-muconate can include, for example, one or more of: methanol, ethanol, propanol, isopropanol, acetic acid, acetonitrile, and acetone, as well as butanols such as 1-butanol and isobutanol, and other alcohols which are not completely miscible with water.

The solvent extraction can be carried out at a pH of below about 4, e.g., at a pH where the cis,trans-muconic acid is sufficiently protonated that it will partition into the organic solvent used for the extraction. Even at pH levels low enough to induce precipitation, a fraction of the protonated cis,trans-muconic acid can remain in solution. For example, and as shown in Table 2 in Example 9 above, at pH 3 about 60% of the cis,trans-muconic acid originally in the solution precipitates and can be separated by filtration. However, the approximately 40% of the cis,trans-muconic acid remaining in solution cannot be separated by filtration but can be recovered by extraction. Accordingly, solvent extraction can increase the isolation yield of cis,trans-muconate relative to a method that does not include extracting the cis,trans-muconic acid from solution using an organic solvent. It is also clear from the data in Table 2 of Example 9 that the extraction of cis,trans-muconate can proceed even if some portion of the cis,trans-muconate has precipitated and is not in the aqueous solution.

The solvent extraction can also include separating the cis, trans-muconate from an inorganic salt (e.g., ammonium sulfate, calcium sulfate). Furthermore, solvent extraction can produce a more pure cis,trans-muconate than precipitation which can also cause the precipitation of, and therefore contamination with, inorganic salts.

Selection of solvent and/or pH parameters can be facilitated by a series of simple measurements. For each potential solvent, extractions can be performed (e.g., to measure partition coefficients) on all three muconic acid isomers (cis,cis-, cis,trans-, and trans,trans-isomers). Each isomer can also be tested against a range of pH values using increments (e.g., 0.5) between about pH 1 and below pH 7.

Example 11

Separation of cis,trans-Muconic Acid from Fermentation Broth by Solvent Extraction Fermentation broth was obtained that had been isomerized to cis,trans-muconic acid, and was acidified to a pH of about 3. The solid cis,trans-muconic acid was removed by filtration to leave acidified fermentation broth containing approximately 5 to 10 grams per Liter of cis,trans-muconic acid.

To individual 50 mL conical centrifuge tubes each containing 15 mL of the filtered broth were added 15 mL of each solvent listed in tables below. Each tube was agitated for two minutes and the organic and aqueous phases allowed to separate. The aqueous layer was separated from the solvent layer by pipette and placed into a new 50 mL conical tube. Both the aqueous and solvent phases of each extraction were analyzed for muconic acid using HPLC. A second extraction was performed on each of the separated aqueous layers using fresh solvent. Again the samples were agitated, allowed to settle and the aqueous and organic phases were separated and analyzed.

The results are shown in Tables 3, 4, and 5 below. Different broth samples with different amounts of cis,trans-muconic acid were used to generate the results in each table.

TABLE 3

Broth containing 9.82 g/L cis,trans-muconic acid.

| Solvent | Extraction number | Muconic acid in organic phase | Muconic acid in aqueous phase | Partition coefficient |
|---|---|---|---|---|
| None | | | 9.82 | |
| tBME | 1 | 6.53 | 2.05 | 3.19 |
| tBME | 2 | 1.23 | 0.72 | 1.71 |
| Octanol | 1 | 5.40 | 2.19 | 2.47 |
| Octanol | 2 | 0.53 | 1.52 | 0.35 |
| 1-butanol | 1 | 6.26 | 1.10 | 5.69 |
| 1-butanol | 2 | 0.51 | 0.27 | 1.89 |

TABLE 4

Broth containing 10.69 g/L cis,trans-muconic acid.

| Solvent | Extraction number | Muconic acid in organic phase | Muconic acid in aqueous phase | Partition coefficient |
|---|---|---|---|---|
| none | | | 10.69 | |
| 1-pentanol | 1 | 8.29 | 1.29 | 6.43 |
| 1-pentanol | 2 | 1.06 | 0.30 | 3.53 |
| cyclohexane | 1 | 0.00 | 10.47 | 0.00 |
| cyclohexane | 2 | 0.00 | 10.20 | 0.00 |
| n-butyl acetate | 1 | 6.78 | 3.96 | 1.71 |
| n-butyl acetate | 2 | 3.55 | 2.02 | 1.76 |
| MEK | 1 | 9.65 | 2.63 | 3.67 |
| MEK | 2 | 1.99 | 0.84 | 2.37 |
| MeTHF | 1 | 7.40 | 0.65 | 11.38 |
| MeTHF | 2 | 0.51 | 0.00 | large |

TABLE 4-continued

Broth containing 10.69 g/L cis,trans-muconic acid.

| Solvent | Extraction number | Muconic acid in organic phase | Muconic acid in aqueous phase | Partition coefficient |
|---|---|---|---|---|
| cylcohexanol | 1 | 8.62 | 0.98 | 8.80 |
| cylcohexanol | 2 | 1.05 | 0.28 | 3.75 |
| decalin | 1 | 0.00 | 10.25 | 0.00 |
| decalin | 2 | 0.00 | 12.99 | 0.00 |

TABLE 5

Broth containing 4.86 g/L cis,trans-muconic acid.

| Solvent | Extraction number | Muconic acid in organic phase | Muconic acid in aqueous phase | Partition coefficient |
|---|---|---|---|---|
| none | | | 4.86 | |
| cyclohexanone | | 6.11 | 0.21 | 29.10 |
| cyclohexanone | | 0.00 | 0.23 | large |
| xylene | | 0.00 | 5.15 | 0.00 |
| xylene | | 0.00 | 4.82 | 0.00 |
| isoalcohol | | 4.87 | 0.63 | 7.73 |
| isoalcohol | | 0.49 | 0.04 | 12.25 |
| ethyl hexanol | | 3.83 | 0.89 | 4.30 |
| ethyl hexanol | | 0.79 | 0.20 | 3.95 |

To test the ability of solvent extraction to recover cis,trans-muconic acid after acidification to sufficiently low levels that significant amounts of the cis,trans-muconic acid has precipitated, a solution of cis,trans-muconic acid in a solution of M9 salts was used to simulate a fermentation broth. 15 grams of cis,trans-muconic acid were added to 250 mL of M9 salts giving an approximate titer of 60 g/L. This was achieved by raising the pH to 7.0 using sodium hydroxide. The broth was then acidified with sulfuric acid to pH 3.0 causing the cis,trans-muconic acid to precipitate. The solid precipitate was left in the acidified mixture, and the entire slurry was extracted twice with solvent as described above. The results are shown in Table 6.

TABLE 6

Broth containing 63.34 g/L cis,trans-muconic acid, including precipitated muconic acid.

| Solvent | Extraction number | Muconic acid in organic phase | Muconic acid in aqueous phase | Partition coefficient |
|---|---|---|---|---|
| none | | | 63.34 | |
| cyclohexanone | 1 | 51.05 | 2.92 | 17.48 |
| cylcohexanone | 2 | 2.10 | 0.20 | 10.50 |
| MeTHF | 1 | 47.10 | 2.03 | 23.20 |
| MeTHF | 2 | 1.64 | 0.11 | 14.91 |
| cyclohexanol | 1 | 51.37 | 10.53 | 4.88 |
| cyclohexanol | 2 | 3.75 | 2.71 | 1.38 |
| tBME | 1 | 0.00 | 54.00 | 0.00 |
| tBME | 2 | 0.00 | 59.88 | 0.00 |

Example 12

Isomerization of cis,trans-Muconic Acid to trans,trans-Muconic Acid Catalyzed by Iodine A mixture containing cis,trans-muconic acid (1.00 g), a catalytic amount of $I_2$ (53 mg), and MeCN (35 ml) was heated to reflux for 11 h. After cooling to room temperature, the precipitated solid was filtered off and washed with cold MeCN. After drying under vacuum, 0.80 g (80% yield) of purified trans,trans-muconic acid was present as a tan-colored powder. The material obtained by this procedure was confirmed to be trans,trans-muconic acid by $^1$H and $^{13}$C NMR spectroscopy. The isomerization reaction proceeded better in nonpolar solvents (e.g., THF) than in a number of other tested solvents.

Example 13

Isomerization of cis,trans-Muconic Acid to trans,trans-Muconic Acid Catalyzed by a Hydrogenation Catalyst A mixture containing cis,trans-muconic acid (1.00 g) and a catalytic amount of palladium supported on carbon (Pd/C, 5%) is prepared in 50 mL of methanol. The methanol reaction mixture is brought to reflux for 1 hour, cooled to room temperature, and then the supported palladium catalyst is removed by filtration. The remaining reaction solution is evaporated to about one-half the original volume, then diluted with one volume of MeCN. Evaporation under reduced pressure is continued until the methanol is removed and the trans,trans-muconic acid begins to fall out of solution. The resulting solid is filtered off and washed with cold MeCN. After drying under vacuum, about 0.80 g (80% yield) of purified trans,trans-muconic acid can be present as a tan-colored powder. The material obtained by this procedure can be confirmed to be trans,trans-muconic acid by $^1$H and $^{13}$C NMR spectroscopy.

Example 14

Isomerization of cis,cis-Muconic Acid to trans,trans-Muconic Acid Catalyzed by a Hydrogenation Catalyst A mixture containing cis,cis-muconic acid (1.00 g) and a catalytic amount of palladium supported on carbon (Pd/C, 5%) is prepared in 50 mL of methanol. The methanol reaction mixture is brought to reflux for 1 hour, cooled to room temperature, and then the supported palladium catalyst is removed by filtration. The remaining reaction solution is evaporated to about one-half the original volume, then diluted with one volume of MeCN. Evaporation under reduced pressure is continued until the methanol is removed and the trans,trans-muconic acid begins to fall out of solution. The resulting solid is filtered off and washed with cold MeCN. After drying under vacuum, about 0.80 g (80% yield) of purified trans,trans-muconic acid can be present as a tan-colored powder. The material obtained by this procedure can be confirmed to be trans,trans-muconic acid by $^1$H and $^{13}$C NMR spectroscopy.

While the invention has been particularly shown and described with reference to specific embodiments, it should be understood by those skilled in the art that various changes in form and detail can be made without departing from the spirit and scope of the invention as defined by the appended claims.

The invention claimed is:
1. A method for producing cis,trans-muconate comprising:
   providing cis,cis-muconate produced from a renewable carbon source through biocatalytic conversion;
   isomerizing cis,cis-muconate to cis, trans-muconate under reaction conditions in which substantially all of the cis,cis-muconate is isomerized to cis,trans-muconate at a pH between about 3.5 and about 4.5;
   extracting the cis,trans-muconate with an organic solvent immiscible with an aqueous phase; and
   crystallizing the cis,trans-muconate.
2. The method of claim 1, further comprising
   culturing recombinant cells that express 3-dehydroshikimate dehydratase, protocatechuate decarboxylase and catechol 1,2-dioxygenase in a medium comprising the renewable carbon source and under conditions in which the renewable carbon source is converted to 3-dehydroshikimate by enzymes in the common pathway of aromatic amino acid biosynthesis of the cell, and the 3-dehydroshikimate is biocatalytically converted to cis,cis-muconate.
3. The method of claim 1, wherein the isomerization reaction is catalyzed by an acid, wherein the acid can be an inorganic acid or an organic acid.
4. The method of claim 1, further comprising precipitating the cis,trans-muconate from solution by acidification to a pH below about 3.0.
5. The method of claim 1, wherein the cis, trans-muconate is crystallized with an organic solvent, wherein the organic solvent comprises one or more of methanol, ethanol, propanol, isopropanol, butanol, acetic acid, acetonitrile, acetone, and tetrahydrofuran.
6. The method of claim 1, wherein the cis, trans-muconate is further isomerized to trans,trans-muconate in a reaction catalyzed by $I_2$, by a precious metal hydrogenation catalyst, by a sponge metal hydrogenation catalyst, or by a skeletal hydrogenation catalyst.
7. A method for producing cis,trans-muconate comprising:
   providing an aqueous fermentation broth comprising cis,cis-muconate produced from a renewable carbon source through biocatalytic conversion;
   isomerizing cis,cis-muconate to cis,trans-muconate under reaction conditions in which substantially all of the cis,cis-muconate is isomerized to cis,trans-muconate at a pH between about 3.5 and about 4.5;
   extracting the cis,trans-muconate from the aqueous broth with an organic solvent immiscible with the aqueous broth; and
   crystallizing the cis,trans-muconate.
8. The method of claim 7, wherein the fermentation broth comprises recombinant cells that express 3-dehydroshikimate dehydratase, protocatechuate decarboxylase and catechol 1,2-dioxygenase.
9. The method of claim 8, further comprising:
   culturing the recombinant cells that express 3-dehydroshikimate dehydratase, protocatechuate decarboxylase and catechol 1,2-dioxygenase in a medium comprising the renewable carbon source and under conditions in which the renewable carbon source is converted to 3-dehydroshikimate by enzymes in the common pathway of aromatic amino acid biosynthesis of the cell, and the 3-dehydroshikimate is biocatalytically converted to cis,cis-muconate,
   wherein the recombinant cells are cultured in a fermentor vessel, thereby producing the fermentation broth.
10. The method of claim 1, wherein providing cis, cis-muconate produced from the renewable carbon source through biocatalytic conversion employs a host cell transfoimed with heterologous structural genes from *Klebsiella pneumoniae*, which express the enzymes 3-dehydroshikimate dehydratase and protocatechuate decarboxylase, and from *Acinetobacter calcoaceticus*, which expresses the enzyme catechol 1,2-dioxygenase.

11. The method of claim 10 wherein the host cell further comprises heterologous DNA sequences which express the enzymes 3-deoxy-D-arabino-heptulosonate 7-phosphate synthase and 3-dehydroquinate synthase.

12. The method of claim 11 wherein the host cell further comprises heterologous DNA sequences which express the enzyme transketolase.

13. The method of claim 10, wherein the host cell is selected from mutant cell lines having mutations in the common pathway of aromatic amino acid biosynthesis that block conversion of 3-dehydroshikimate to chorismate.

14. The method of claim 10, wherein the host cell produces cis,cis-muconic acid at a rate of at least about 0.95 millimoles/liter/hour.

15. The method of claim 1, wherein providing cis,cis-muconate produced from the renewable carbon source through biocatalytic conversion comprises culturing a transformed host cell, which expresses heterologous structural genes encoding 3-dehydroshikimate dehydratase, protocatechuate decarboxylase, catechol 1,2-dioxygenase, transketolase, 3-deoxy-D-arabino-heptulosonate 7-phosphate synthase, and 3-dehydroquinate synthase, in a medium containing a carbon source which is converted to 3-dehydroshikimate, by the enzymes in the common pathway of aromatic amino acid biosynthesis of the host cell.

16. The method of claim 1, wherein the renewable carbon source is a biospheric feedstock.

17. The method of claim 2, wherein the recombinant cells are recombinant prokaryotic or eukaryotic cells.

18. The method of claim 7, wherein the renewable carbon source is a biospheric feedstock.

19. The method of claim 8, wherein the recombinant cells are recombinant prokaryotic or eukaryotic cells.

20. The method of claim 1, wherein the organic solvent is selected from the group consisting of: methyl isobutylketone, ethyl acetate, isopropyl acetate, heptanes, methyl tert-butylether, methylene chloride, methyl ethyl ketone, cyclohexanol, tetralin, tetralone, butyl acetate, methyl tetrahydrofuran, cyclohexanone, octanol, butanol, pentanol, isoamyl alcohol, and 2-ethylhexanol.

21. The method of claim 7, wherein the organic solvent is selected from the group consisting of: methyl isobutylketone, ethyl acetate, isopropyl acetate, heptanes, methyl tert-butylether, methylene chloride, methyl ethyl ketone, cyclohexanol, tetralin, tetralone, butyl acetate, methyl tetrahydrofuran, cyclohexanone, octanol, butanol, pentanol, isoamyl alcohol, and 2-ethylhexanol.

22. The method of claim 7, further comprising precipitating the cis,trans-muconate from the broth by acidification to a pH below about 3.0.

* * * * *

UNITED STATES PATENT AND TRADEMARK OFFICE
CERTIFICATE OF CORRECTION

PATENT NO.         : 8,809,583 B2
APPLICATION NO.    : 13/518534
DATED              : August 19, 2014
INVENTOR(S)        : Vu Bui et al.

Page 1 of 1

It is certified that error appears in the above-identified patent and that said Letters Patent is hereby corrected as shown below:

In the claims:

In claim 10 at column 26, lines 62-63, replace "transfoimed" with --transformed--.

Signed and Sealed this
Twenty-third Day of December, 2014

Michelle K. Lee
*Deputy Director of the United States Patent and Trademark Office*